(12) United States Patent
Takahashi et al.

(10) Patent No.: US 9,708,382 B2
(45) Date of Patent: Jul. 18, 2017

(54) PEPTIDE LIBRARY

(71) Applicant: Daiichi Sankyo Company, Limited, Tokyo (JP)

(72) Inventors: Tohru Takahashi, Tokyo (JP); Naoya Shinozaki, Tokyo (JP); Takeshi Takizawa, Tokyo (JP); Takako Kimura, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 0 days.

(21) Appl. No.: 13/956,916

(22) Filed: Aug. 1, 2013

(65) Prior Publication Data

US 2013/0316929 A1 Nov. 28, 2013

Related U.S. Application Data

(63) Continuation of application No. PCT/JP2012/052304, filed on Feb. 1, 2012.

(30) Foreign Application Priority Data

Feb. 2, 2011 (JP) ................ 2011-020559

(51) Int. Cl.
*C40B 40/10* (2006.01)
*C07K 14/715* (2006.01)
*C07K 14/525* (2006.01)
*C40B 40/02* (2006.01)

(52) U.S. Cl.
CPC ........ *C07K 14/525* (2013.01); *C07K 14/7151* (2013.01); *C40B 40/10* (2013.01); *C40B 40/02* (2013.01)

(58) Field of Classification Search
None
See application file for complete search history.

(56) References Cited

U.S. PATENT DOCUMENTS

2008/0181886 A1* 7/2008 Kelley .................. 424/133.1

FOREIGN PATENT DOCUMENTS

| WO | 01/85781 | 11/2001 |
| WO | WO 01/85782 | 11/2001 |
| WO | 2006/052493 | 5/2006 |

OTHER PUBLICATIONS

Web page printouts from http://www.ncbi.nlm.nih.gov/snp for TACI (TNFRSF13B) SNPs rs546335485, rs72553877, rs368250378 and rs549493928, obtained Feb. 11, 2016.*
Lehninger, L., Biochemistry, 2nd edition, pp. 73-75, Worth Publisher, New York (1975).
Gluzman, Y. "SV40-transformed simian cells support the replication of early SV40 mutants", Cell (1981), vol. 23, pp. 175-182.

(Continued)

*Primary Examiner* — Karen S Weiler
(74) *Attorney, Agent, or Firm* — Locke Lord LLP

(57) ABSTRACT

The present invention provides a peptide library comprising a plurality of mutant peptides based on the extracellular binding domain of the TACI protein. The mutant peptides of the library have the capacity to bind to target molecules other than the endogenous TACI ligands. The present invention further provides a peptide library comprising a plurality of mutant peptides each comprising an amino acid sequence of SEQ ID NO: 1 in the Sequence Listing.

5 Claims, 8 Drawing Sheets

(56) References Cited

OTHER PUBLICATIONS

Urlaub, G., and Chasin, L.A., "Isolation of Chinese hamster cell mutants deficient in dihydrofolate reductase activity", PNAS 77(7) 4216-4220 (1980).

Saiki, R.K., et al. "Primer-directed enzymatic amplification of DNA with a thermostable DNA polymerase", Science 239 (4839):487-91 (1988).

"Fmoc Solid Phase Peptide Synthesis—A Practical Approach", W. C. Chan, P. D. White Eds., Oxford University Press, New York, 2000.

Keefe, A.D., et al. "Functional proteins from a random-sequence library", Nature 410, 715-718 (2001).

Yamaguchi, J., et al. "cDNA display: a novel screening method for functional disulfide-rich peptides by solid-phase synthesis and stabilization of mRNA-protein fusions" Nucl. Acids Res. 37 (16): e108 (2009).

Hymowitz, S.G., et al. "Structures of APRIL-Receptor Complexes: Like BCMA, TACI employs only a single cysteine-rich domain for high affinity ligand binding", J. Biol. Chem. 280(1): 7218-7227 (2005).

Fried, A.J., et al. "Functional analysis of transmembrane activator and calcium-modulating cyclophilin ligand interactor (TACI) mutations associated with common variable immunodeficiency", Journal of Allergy and Clinical Immunology 128(1): 226-228 (2011).

International Preliminary Report on Patentability for corresponding International PCT Application No. PCT/JP2012/052304; dated Aug. 6, 2013.

Written Opinion of the International Searching Authority for corresponding International PCT Application No. PCT/JP2012/052304; dated Mar. 13, 2012.

International Search Report for corresponding International PCT Application No. PCT/JP2012/052304; dated Mar. 13, 2012.

Supplementary European Search Report and European Search Opinion as issued in Corresponding EP Application No. 12742385.3, dated Nov. 19, 2014.

\* cited by examiner (3)

| Target | | S L S C R K E Q G K | X | Y | X X X X X | D | C | X | S C A S | X | C G | X | H P | X X | C A Y F C E N | SEQ ID NO |
|---|---|---|---|---|---|---|---|---|---|---|---|---|---|---|---|---|
| | WT | S L S C R K E Q G K | F | Y | D H L L R | D | C | I | S C A S | I | C G | Q | H P | K Q | C A Y F C E N | 22 |
| BSA | 1 | - - - - - - - - - - | Q | - | W R E K M | - | - | E | * - - - | K | - - | N | - - | D I | - - - - - - - | 2 |
| EphA2 | 2 | - - - - - - - - - - | Q | - | L L R E W | - | - | D | - - - - | E | - - | S | - - | H Y | - - - - - - - | 3 |
| | 3 | - - - - - - - - - - | M | - | L L K E W | - | - | A | - - - - | A | - - | N | - - | H Y | - - - - - - - | 4 |
| | 4 | - - - - - - - - - - | H | - | L L K E Y | - | - | D | - - - - | E | - - | Y | - - | D Y | - - - - - - - | 5 |
| EGFR-Fc | 5 | - - - - - - - - - - | S | - | G A I M Y | - | - | S | - - - - | Y | - - | E | - - | W H | - - - - - - - | 6 |
| | 6 | - - - - - - - - - - | E | - | G A I A W | - | - | S | - - - - | Y | - - | A | - - | F E | - - - - - - - | 7 |
| | 7 | - - - - - - - - - - | N | - | I H Q Q W | - | - | A | - - - - | E | - - | G | - - | N Y | - - - - - - - | 8 |
| VEGF | 8 | - - - - - - - - - - | W | - | M T W E S | - | - | K | - - - - | W | - - | S | - - | F D | - - - - - - - | 9 |
| | 9 | - - - - - - - - - - | M | - | D L Y G F | - | - | R | - - - - | M | - - | K | - - | D L | - - - - - - - | 10 |
| | 10 | - - - - - - - - - - | M | - | M V W T Q | - | - | K | - - - - | W | - - | A | - - | V A | - - - - - - - | 11 |
| | 11 | - - - - - - - - - - | I | - | N Q Y G F | - | - | K | - - - - | W | - - | K | - - | D M | - - - - - - - | 12 |
| | 12 | - - - - - - - - - - | I | - | M T W H D | - | - | H | - - - - | L | - - | S | - - | L F | - - - - - - - | 13 |
| | 13 | - - - - - - - - - - | D | - | M V F G Q | - | - | H | - - - - | W | - - | K | - - | V A | - - - - - - - | 14 |
| TNF-α | 14 | - - - - - - - - - - | Q | - | M A G H F | - | - | N | - - - - | R Y | - | H | - - | L M | - - - - - - - | 15 |
| | 15 | - - - - - - - D - | T | - | I E Y G F | - | - | R | - - - - | G | - - | G | - - | L M | - - - - - - - | 16 |
| | 16 | - - - - - - - - - - | S | - | T S E W F | - | - | A | - - - - | K Y | - | K | - - | L V | - - - - - - - | 17 |

X: Mutation position

SEQUENCE LISTING

```
<160> NUMBER OF SEQ ID NOS: 22

<210> SEQ ID NO 1
<211> LENGTH: 39
<212> TYPE: PRT
<213> ORGANISM: Artificial Sequence
<220> FEATURE:
<223> OTHER INFORMATION: Amino acid sequence of human TACI_d2 peptide
<220> FEATURE:
<221> NAME/KEY: SITE
<222> LOCATION: (11)..(11)
<223> OTHER INFORMATION: Any amino acid
<220> FEATURE:
<221> NAME/KEY: SITE
<222> LOCATION: (13)..(17)
<223> OTHER INFORMATION: Any amino acid
<220> FEATURE:
<221> NAME/KEY: SITE
<222> LOCATION: (20)..(20)
<223> OTHER INFORMATION: Any amino acid
<220> FEATURE:
```

```
<221> NAME/KEY: SITE
<222> LOCATION: (25)..(25)
<223> OTHER INFORMATION: Any amino acid
<220> FEATURE:
<221> NAME/KEY: SITE
<222> LOCATION: (28)..(28)
<223> OTHER INFORMATION: Any amino acid
<220> FEATURE:
<221> NAME/KEY: SITE
<222> LOCATION: (31)..(32)
<223> OTHER INFORMATION: Any amino acid

<400> SEQUENCE: 1

Ser Leu Ser Cys Arg Lys Glu Gln Gly Lys Xaa Tyr Xaa Xaa Xaa Xaa
1               5                   10                  15

Xaa Asp Cys Xaa Ser Cys Ala Ser Xaa Cys Gly Xaa His Pro Xaa Xaa
                20                  25                  30

Cys Ala Tyr Phe Cys Glu Asn
            35

<210> SEQ ID NO 2
<211> LENGTH: 38
<212> TYPE: PRT
<213> ORGANISM: Artificial Sequence
<220> FEATURE:
<223> OTHER INFORMATION: Amino acid sequence of human BSA-binding
      peptide

<400> SEQUENCE: 2

Ser Leu Ser Cys Arg Lys Glu Gln Gly Lys Gln Tyr Trp Arg Glu Lys
1               5                   10                  15

Met Asp Cys Glu Cys Ala Ser Lys Cys Gly Asn His Pro Asp Ile Cys
                20                  25                  30

Ala Tyr Phe Cys Glu Asn
            35

<210> SEQ ID NO 3
<211> LENGTH: 39
<212> TYPE: PRT
<213> ORGANISM: Artificial Sequence
<220> FEATURE:
<223> OTHER INFORMATION: Amino acid sequence of human EphA2-binding
      peptide a-EphA2 #1

<400> SEQUENCE: 3

Ser Leu Ser Cys Arg Lys Glu Gln Gly Lys Gln Tyr Leu Leu Arg Glu
1               5                   10                  15

Trp Asp Cys Asp Ser Cys Ala Ser Glu Cys Gly Ser His Pro His Tyr
                20                  25                  30

Cys Ala Tyr Phe Cys Glu Asn
            35

<210> SEQ ID NO 4
<211> LENGTH: 39
<212> TYPE: PRT
<213> ORGANISM: Artificial Sequence
<220> FEATURE:
<223> OTHER INFORMATION: Amino acid sequence of human EphA2-binding
      peptide a-EphA2 #2

<400> SEQUENCE: 4

Ser Leu Ser Cys Arg Lys Glu Gln Gly Lys Met Tyr Leu Leu Lys Glu
1               5                   10                  15

Trp Asp Cys Ala Ser Cys Ala Ser Ala Cys Gly Asn His Pro His Tyr
                20                  25                  30
```

```
Cys Ala Tyr Phe Cys Glu Asn
         35

<210> SEQ ID NO 5
<211> LENGTH: 39
<212> TYPE: PRT
<213> ORGANISM: Artificial Sequence
<220> FEATURE:
<223> OTHER INFORMATION: Amino acid sequence of human EphA2-binding
      peptide a-EphA2 #3

<400> SEQUENCE: 5

Ser Leu Ser Cys Arg Lys Glu Gln Gly Lys His Tyr Leu Leu Lys Glu
1               5                   10                  15

Tyr Asp Cys Asp Ser Cys Ala Ser Glu Cys Gly Tyr His Pro Asp Tyr
            20                  25                  30

Cys Ala Tyr Phe Cys Glu Asn
         35

<210> SEQ ID NO 6
<211> LENGTH: 39
<212> TYPE: PRT
<213> ORGANISM: Artificial Sequence
<220> FEATURE:
<223> OTHER INFORMATION: Amino acid sequence of human EGFR-binding
      peptide (1)

<400> SEQUENCE: 6

Ser Leu Ser Cys Arg Lys Glu Gln Gly Lys Ser Tyr Gly Ala Ile Met
1               5                   10                  15

Tyr Asp Cys Ser Ser Cys Ala Ser Tyr Cys Gly Glu His Pro Trp His
            20                  25                  30

Cys Ala Tyr Phe Cys Glu Asn
         35

<210> SEQ ID NO 7
<211> LENGTH: 39
<212> TYPE: PRT
<213> ORGANISM: Artificial Sequence
<220> FEATURE:
<223> OTHER INFORMATION: - Amino acid sequence of human EGFR-binding
      peptide (2)

<400> SEQUENCE: 7

Ser Leu Ser Cys Arg Lys Glu Gln Gly Lys Glu Tyr Gly Ala Ile Ala
1               5                   10                  15

Trp Asp Cys Ser Ser Cys Ala Ser Tyr Cys Gly Ala His Pro Phe Glu
            20                  25                  30

Cys Ala Tyr Phe Cys Glu Asn
         35

<210> SEQ ID NO 8
<211> LENGTH: 39
<212> TYPE: PRT
<213> ORGANISM: Artificial Sequence
<220> FEATURE:
<223> OTHER INFORMATION: Amino acid sequence of human EGFR-binding
      peptide (3)

<400> SEQUENCE: 8

Ser Leu Ser Cys Arg Lys Glu Gln Gly Lys Asn Tyr Ile His Gln Gln
1               5                   10                  15

Trp Asp Cys Ala Ser Cys Ala Ser Glu Cys Gly Gly His Pro Asn Tyr
```

Cys Ala Tyr Phe Cys Glu Asn
        35

<210> SEQ ID NO 9
<211> LENGTH: 39
<212> TYPE: PRT
<213> ORGANISM: Artificial Sequence
<220> FEATURE:
<223> OTHER INFORMATION: Amino acid sequence of human VEGF-binding
      peptide (1)

<400> SEQUENCE: 9

Ser Leu Ser Cys Arg Lys Glu Gln Gly Lys Trp Tyr Met Thr Trp Glu
1               5                   10                  15

Ser Asp Cys Lys Ser Cys Ala Ser Trp Cys Gly Ser His Pro Phe Asp
            20                  25                  30

Cys Ala Tyr Phe Cys Glu Asn
        35

<210> SEQ ID NO 10
<211> LENGTH: 39
<212> TYPE: PRT
<213> ORGANISM: Artificial Sequence
<220> FEATURE:
<223> OTHER INFORMATION: Amino acid sequence of human VEGF-binding
      peptide (2)

<400> SEQUENCE: 10

Ser Leu Ser Cys Arg Lys Glu Gln Gly Lys Met Tyr Asp Leu Tyr Gly
1               5                   10                  15

Phe Asp Cys Arg Ser Cys Ala Ser Met Cys Gly Lys His Pro Asp Leu
            20                  25                  30

Cys Ala Tyr Phe Cys Glu Asn
        35

<210> SEQ ID NO 11
<211> LENGTH: 39
<212> TYPE: PRT
<213> ORGANISM: Artificial Sequence
<220> FEATURE:
<223> OTHER INFORMATION: Amino acid sequence of human VEGF-binding
      peptide (3)

<400> SEQUENCE: 11

Ser Leu Ser Cys Arg Lys Glu Gln Gly Lys Met Tyr Met Val Trp Thr
1               5                   10                  15

Gln Asp Cys Lys Ser Cys Ala Ser Trp Cys Gly Ala His Pro Val Ala
            20                  25                  30

Cys Ala Tyr Phe Cys Glu Asn
        35

<210> SEQ ID NO 12
<211> LENGTH: 39
<212> TYPE: PRT
<213> ORGANISM: Artificial Sequence
<220> FEATURE:
<223> OTHER INFORMATION: Amino acid sequence of human VEGF-binding
      peptide (4)

<400> SEQUENCE: 12

Ser Leu Ser Cys Arg Lys Glu Gln Gly Lys Ile Tyr Asn Gln Tyr Gly
1               5                   10                  15

```
Phe Asp Cys Lys Ser Cys Ala Ser Trp Cys Gly Lys His Pro Asp Met
                20                  25                  30

Cys Ala Tyr Phe Cys Glu Asn
        35

<210> SEQ ID NO 13
<211> LENGTH: 39
<212> TYPE: PRT
<213> ORGANISM: Artificial Sequence
<220> FEATURE:
<223> OTHER INFORMATION: Amino acid sequence of human VEGF-binding
      peptide (5)

<400> SEQUENCE: 13

Ser Leu Ser Cys Arg Lys Glu Gln Gly Lys Ile Tyr Met Thr Trp His
1               5                   10                  15

Asp Asp Cys His Ser Cys Ala Ser Leu Cys Gly Ser His Pro Leu Phe
                20                  25                  30

Cys Ala Tyr Phe Cys Glu Asn
        35

<210> SEQ ID NO 14
<211> LENGTH: 39
<212> TYPE: PRT
<213> ORGANISM: Artificial Sequence
<220> FEATURE:
<223> OTHER INFORMATION: Amino acid sequence of human VEGF-binding
      peptide (6)

<400> SEQUENCE: 14

Ser Leu Ser Cys Arg Lys Glu Gln Gly Lys Asp Tyr Met Val Phe Gly
1               5                   10                  15

Gln Asp Cys His Ser Cys Ala Ser Trp Cys Gly Lys His Pro Val Ala
                20                  25                  30

Cys Ala Tyr Phe Cys Glu Asn
        35

<210> SEQ ID NO 15
<211> LENGTH: 39
<212> TYPE: PRT
<213> ORGANISM: Artificial Sequence
<220> FEATURE:
<223> OTHER INFORMATION: Amino acid sequence of human TNFa-binding
      peptide (1)

<400> SEQUENCE: 15

Ser Leu Ser Cys Arg Lys Glu Gln Gly Lys Gln Tyr Met Ala Gly His
1               5                   10                  15

Phe Asp Cys Asn Ser Cys Ala Ser Arg Tyr Gly His His Pro Leu Met
                20                  25                  30

Cys Ala Tyr Phe Cys Glu Asn
        35

<210> SEQ ID NO 16
<211> LENGTH: 39
<212> TYPE: PRT
<213> ORGANISM: Artificial Sequence
<220> FEATURE:
<223> OTHER INFORMATION: Amino acid sequence of human TNFa-binding
      peptide (2)

<400> SEQUENCE: 16

Ser Leu Ser Cys Arg Lys Glu Gln Asp Lys Thr Tyr Ile Glu Tyr Gly
1               5                   10                  15
```

Phe Asp Cys Arg Ser Cys Ala Ser Gly Cys Gly Gly His Pro Leu Met
            20                  25                  30

Cys Ala Tyr Phe Cys Glu Asn
        35

<210> SEQ ID NO 17
<211> LENGTH: 39
<212> TYPE: PRT
<213> ORGANISM: Artificial Sequence
<220> FEATURE:
<223> OTHER INFORMATION: Amino acid sequence of human TNFa-binding
      peptide (3)

<400> SEQUENCE: 17

Ser Leu Ser Cys Arg Lys Glu Gln Gly Lys Ser Tyr Thr Ser Glu Trp
1               5                   10                  15

Phe Asp Cys Ala Ser Cys Ala Ser Lys Tyr Gly Lys His Pro Leu Val
            20                  25                  30

Cys Ala Tyr Phe Cys Glu Asn
        35

<210> SEQ ID NO 18
<211> LENGTH: 183
<212> TYPE: DNA
<213> ORGANISM: Artificial Sequence
<220> FEATURE:
<223> OTHER INFORMATION: Nucleotide sequence of randomly mutated
      TACI_d2 oligonucleotide
<220> FEATURE:
<221> NAME/KEY: misc_feature
<222> LOCATION: (68)..(70)
<223> OTHER INFORMATION: n is a, c, g, or t
<220> FEATURE:
<221> NAME/KEY: misc_feature
<222> LOCATION: (74)..(88)
<223> OTHER INFORMATION: n is a, c, g, or t
<220> FEATURE:
<221> NAME/KEY: misc_feature
<222> LOCATION: (95)..(97)
<223> OTHER INFORMATION: n is a, c, g, or t
<220> FEATURE:
<221> NAME/KEY: misc_feature
<222> LOCATION: (110)..(112)
<223> OTHER INFORMATION: n is a, c, g, or t
<220> FEATURE:
<221> NAME/KEY: misc_feature
<222> LOCATION: (119)..(121)
<223> OTHER INFORMATION: n is a, c, g, or t
<220> FEATURE:
<221> NAME/KEY: misc_feature
<222> LOCATION: (128)..(133)
<223> OTHER INFORMATION: n is a, c, g, or t

<400> SEQUENCE: 18
gctgcacact gtaggagaag actgggccca gccggccagc ctgagttgcc gtaaagaaca     60
gggcaagnnn tatnnnnnnn nnnnnnnnga ctgcnnnagc tgcgcgagcn nntgtggann    120
ncatcctnnn nnntgcgcgt attttgcga aaacgcggcc gcgagtccac gttccatcgg    180
tca                                                                 183

<210> SEQ ID NO 19
<211> LENGTH: 25
<212> TYPE: DNA
<213> ORGANISM: Artificial Sequence
<220> FEATURE:
<223> OTHER INFORMATION: Nucleotide sequence of PCR primer Primer
      Forward 1

```
<400> SEQUENCE: 19
gctgcacact gtaggagaag actgg                                      25

<210> SEQ ID NO 20
<211> LENGTH: 21
<212> TYPE: DNA
<213> ORGANISM: Artificial Sequence
<220> FEATURE:
<223> OTHER INFORMATION: Nucleotide sequence of PCR primer Primer
      Reverse 1

<400> SEQUENCE: 20
tgaccgatgg aacgtggact c                                          21

<210> SEQ ID NO 21
<211> LENGTH: 23
<212> TYPE: DNA
<213> ORGANISM: Artificial Sequence
<220> FEATURE:
<223> OTHER INFORMATION: Nucleotide sequence of pCANTAB-S1 primer as
      primer for sequencing

<400> SEQUENCE: 21
caacgtaaaa aattattatt cgc                                        23

<210> SEQ ID NO 22
<211> LENGTH: 39
<212> TYPE: PRT
<213> ORGANISM: Artificial Sequence
<220> FEATURE:
<223> OTHER INFORMATION: Amino acid sequence of human TACI_d2 peptide

<400> SEQUENCE: 22

Ser Leu Ser Cys Arg Lys Glu Gln Gly Lys Phe Tyr Asp His Leu Leu
1               5                   10                  15

Arg Asp Cys Ile Ser Cys Ala Ser Ile Cys Gly Gln His Pro Lys Gln
            20                  25                  30

Cys Ala Tyr Phe Cys Glu Asn
        35
```

PEPTIDE LIBRARY

This application is a continuation of International Application No. PCT/JP2012/052304, filed on Feb. 1, 2012, entitled "PEPTIDE LIBRARY", which claims the benefit of Japanese Patent Application Number JP 2011-020559, filed on Feb. 2, 2011, both of which are hereby incorporated by reference.

FIELD OF INVENTION

The present invention relates to a peptide, a derivative of the peptide, a nucleic acid encoding the amino acid sequence of the peptide or the derivative of the peptide, a vector comprising the nucleic acid, a cell harboring the vector or the nucleic acid, a method for producing the peptide or the derivative thereof comprising culturing the cell, a peptide library comprising the peptide and/or the derivative thereof, a method for identifying a peptide and/or a derivative thereof binding to a target molecule, a method for producing a peptide or a derivative thereof that binds to a target molecule, a method for determining whether or not a test peptide or derivative thereof binds to a target molecule, a nucleic acid library comprising the nucleic acid, a composition comprising the peptide or the derivative thereof, the nucleic acid, the vector, or the cell, a reagent comprising the peptide or the derivative thereof, the nucleic acid, the vector, or the cell, etc.

BACKGROUND OF THE INVENTION

TACI, a member of the TNF superfamily, is known to function as a key regulator of B cells. TACI has two cysteine-rich domains (hereinafter, referred to as "CRDs") in its extracellular region and binds to two ligands (APRIL and BAFF). TACI lacking N-terminal CRD as a result of alternative splicing is also found in nature. Reportedly, TACI C-terminal CDR (TACI_d2) alone exhibits binding activity against both the ligands that is equivalent to the binding activity of the whole extracellular region (TACI_d1d2) (See International Publication No. WO 2006/052493; Melissa A. Starovasnik, J. Biol. Chem., vol. 280 (No. 8), pp. 7218-7227 (2005).)

However, whether or not TACI_d2 or a variant thereof exhibits high binding activity against a molecule other than the endogenous ligands has not yet been revealed.

SUMMARY OF THE INVENTION

Technical Problem

The present inventors have conducted diligent studies on TACI_d2 or a variant thereof, and consequently completed the present invention, for example, by preparing a library comprising a peptide that exhibits high binding activity against a molecule other than the endogenous ligands.

Solution to Problem

The present invention relates to:
(1)
 a peptide selected from the following (i) and (ii):
(i) a peptide having the amino acid sequence represented by SEQ ID NO: 1 in the Sequence Listing; and
(ii) a peptide having an amino acid sequence derived from the amino acid sequence represented by SEQ ID NO: 1 in the Sequence Listing, by the conservative amino acid substitution, deletion, addition, or insertion of 1 to 28 (inclusive) amino acids except at the 1st Xaa to the 11th Xaa counting from the amino terminus;
(2)
 the peptide according to (1), wherein each of the 1st Xaa to the 11th Xaa counting from the amino terminus is any amino acid other than cysteine;
(3)
 the peptide according to (1) or (2), wherein each of the 1st Xaa to the 11th Xaa counting from the amino terminus is any amino acid other than proline;
(4)
 the peptide according to any one of (1) to (3), wherein the conservative amino acid substitution is within any group selected from a hydrophobic amino acid group, a neutral hydrophilic amino acid group, an acidic amino acid group, a basic amino acid group, a group of amino acids influencing the direction of the main chain, and an aromatic amino acid group;
(5)
 the peptide according to any one of (1) to (4), wherein the 1st Xaa counting from the amino terminus is an amino acid selected from the group consisting of glutamine, methionine, histidine, serine, glutamic acid, asparagine, tryptophan, isoleucine, aspartic acid, and threonine;
(6)
 the peptide according to any one of (1) to (5), wherein the 2nd Xaa counting from the amino terminus is an amino acid selected from the group consisting of tryptophan, leucine, glycine, isoleucine, methionine, aspartic acid, asparagine, and threonine;
(7)
 the peptide according to any one of (1) to (6), wherein the 3rd Xaa counting from the amino terminus is an amino acid selected from the group consisting of arginine, leucine, alanine, histidine, threonine, valine, glutamine, glutamic acid, and serine;
(8)
 the peptide according to any one of (1) to (7), wherein the 4th Xaa counting from the amino terminus is an amino acid selected from the group consisting of glutamic acid, arginine, lysine, isoleucine, glutamine, tryptophan, tyrosine, glycine, and phenylalanine;
(9)
 the peptide according to any one of (1) to (8), wherein the 5th Xaa counting from the amino terminus is an amino acid selected from the group consisting of lysine, glutamic acid, methionine, alanine, glutamine, glycine, threonine, histidine, and tryptophan;
(10)
 the peptide according to any one of (1) to (9), wherein the 6th Xaa counting from the amino terminus is an amino acid selected from the group consisting of methionine, tryptophan, tyrosine, serine, phenylalanine, glutamine, and aspartic acid;
(11)
 the peptide according to any one of (1) to (10), wherein the 7th Xaa counting from the amino terminus is an amino acid selected from the group consisting of glutamic acid, aspartic acid, alanine, serine, lysine, arginine, histidine, and asparagine;
(12)
 the peptide according to any one of (1) to (11), wherein the 8th Xaa counting from the amino terminus is an amino acid selected from the group consisting of lysine, glutamic acid, alanine, tyrosine, tryptophan, methionine, leucine, arginine, and glycine;

(13) the peptide according to any one of (1) to (12), wherein the 9th Xaa counting from the amino terminus is an amino acid selected from the group consisting of asparagine, serine, tyrosine, glutamic acid, alanine, glycine, lysine, and histidine;

(14) the peptide according to any one of (1) to (13), wherein the 10th Xaa counting from the amino terminus is an amino acid selected from the group consisting of aspartic acid, histidine, tryptophan, phenylalanine, asparagine, valine, and leucine;

(15) the peptide according to any one of (1) to (14), wherein the 11th Xaa counting from the amino terminus is an amino acid selected from the group consisting of isoleucine, tyrosine, histidine, glutamic acid, aspartic acid, leucine, alanine, methionine, phenylalanine, and valine;

(16) the peptide according to any one of (1) to (15), wherein the peptide has the amino acid sequence represented by any one of SEQ ID NOs: 2 to 17 in the Sequence Listing;

(17) a derivative of the peptide according to any one of (1) to (16), the derivative being prepared by chemically modifying or biologically modifying the peptide;

(18) a nucleic acid described in any one of the following (i) to (iii):
(i) a nucleic acid comprising a nucleic acid consisting of a nucleotide sequence encoding the amino acid sequence of the peptide according to any one of (1) to (16);
(ii) a nucleic acid comprising a nucleotide sequence encoding the amino acid sequence of the peptide according to any one of (1) to (16); and
(iii) a nucleic acid consisting of a nucleotide sequence encoding the amino acid sequence of the peptide according to any one of (1) to (16);

(19) a vector comprising the nucleic acid according to any one of (18)(i) to (iii);

(20) a cell harboring the nucleic acid according to any one of (18) (i) to (iii) or a vector according to (19);

(21) a method for producing the peptide according to any one of (1) to (16), the method comprising the following steps (i) and (ii):
(i) culturing the cell according to (20); and
(ii) recovering the peptide from the culture obtained in step (i);

(22) a peptide library comprising the peptide according to any one of (1) to (16) and/or the peptide derivative according to (17);

(23) the library according to (22), wherein the peptide and/or the peptide derivative are prepared by a method comprising steps (i) and (ii) according to (21);

(24) the library according to (22) or (23), wherein in the library, the peptide or the peptide derivative as a phenotype is linked directly or indirectly to a nucleic acid having a genotype corresponding to the phenotype;

(25) the library according to any one of (22) to (24), wherein the nucleic acid is a nucleic acid according to any one of (18)(i) to (iii);

(26) the library according to any one of (22) to (25), wherein the library is a phage display library, a ribosome display library, or a nucleic acid display library;

(27) a method for identifying the peptide according to any one of (1) to (16) or a derivative of the peptide according to (17) binding to a target molecule, comprising the following steps (i) and (ii):
(i) contacting peptides or derivatives of the peptides contained in a library according to any one of (22) to (26) with the target molecule; and
(ii) recovering the peptide or a peptide derivative binding to the target molecule;

(28) a method for producing the peptide according to any one of (1) to (16) or a derivative of the peptide according to (17), that binds to a target molecule, comprising the following steps (i) to (iii):
(i) contacting peptides or derivatives of the peptides contained in a library according to any one of (22) to (26) with the target molecule;
(ii) recovering the peptide or a derivative of the peptide binding to the target molecule; and
(iii) preparing, by chemical synthesis, gene recombination, or in vitro translation, the peptide recovered in step (ii) or the peptide derivative recovered in step (ii);

(29) a method for determining whether or not the peptide according to any one of (1) to (16) or the derivative of the peptide according to (17) binds to a target molecule, comprising the following steps (i) and (ii):
(i) contacting test peptides according to any one of (1) to (16) or test derivatives of the peptides according to (17) with the target molecule; and
(ii) determining that the test peptide or the test derivative of the peptide is positive for binding, when the test peptide or the test derivative of the peptide binds to the target molecule;

(30) a method for producing the peptide according to any one of (1) to (16) or the derivative of the peptide according to (17) that binds to a target molecule, the method comprising the following steps (i) to (iii):
(i) contacting test peptides according to any one of (1) to (16) or test derivatives of the peptides according to (17) with the target molecule;
(ii) determining that the test peptide or the test derivative of the peptide is positive for binding, when the test peptide or the test derivative of the peptide binds to the target molecule; and
(iii) when the test peptide or derivative of the peptide has been determined to be positive in step (ii), preparing the peptide or the derivative of the peptide by chemical synthesis, gene recombination, or in vitro translation;

(31) a nucleic acid library comprising the nucleic acid according to any one of (18)(i) to (iii);

(32) the library according to (31), wherein the nucleic acid is present in a phagemid, a cosmid, or a plasmid, or a fragment thereof;

(33)
the nucleic acid library according to (31) or (32), wherein the nucleic acid is present in a prokaryotic or eukaryotic cell, on viral DNA or RNA, or in a viral particle;
(34)
a composition comprising the peptide according to any one of (1) to (16), the derivative of the peptide according to (17), the nucleic acid according to any one of (18)(i) to (iii), the vector according to (19), or the cell according to (20); and
(35)
a reagent comprising the peptide according to any one of (1) to (16), the derivative of the peptide according to (17), the nucleic acid according to any one of (18)(i) to (iii), the vector according to (19), or the cell according to (20); etc.

Advantageous Effects of Invention

The present invention provides a peptide library useful in screening for a peptide binding to a desired target molecule.

BRIEF DESCRIPTION OF DRAWINGS

FIGS. 1(A)(1) and 1(A)(2) show examples of polyclones.

FIGS. 1(B)(3) and 1(B)(4) show examples of polyclones.

FIGS. 1(C)(5) and 1(C)(6) show examples of single clones.

FIGS. 3(A)(1) and 3(A)(2) show results of assaying α-EphA2 TACI_d2 #1 (α-EphA2 #1) and α-EphA2 TACI_d2 #2 (α-EphA2 #2), respectively. Human EphA2-expressing cells (a) and human ErbB2-expressing cells (b) were each used as cells to be compared. α-EphA2 TACI_d2 #1 and #2 (α-EphA2 #1 and α-EphA2 #2) specifically bound to human EphA2-expressing cells.

FIGS. 3(B)(3) and 3(B)(4) show results of assaying α-EphA2 TACI_d2 #3 (α-EphA2 #3) and wild-type TACI_d2 (WT), respectively. Human EphA2-expressing cells (a) and human ErbB2-expressing cells (b) were each used as cells to be compared.

FIG. 4 is a list of the amino acid sequences of TACI_d2 mutants that specifically bind to target molecules. The *-marked portion indicates that a corresponding amino acid Ser is absent (deleted). WT represents a wild-type amino acid sequence. X (-marked portion) corresponds to (the position of) Xaa in the amino acid sequence represented by SEQ ID NO: 1.

DETAILED DESCRIPTION

Figure 1:
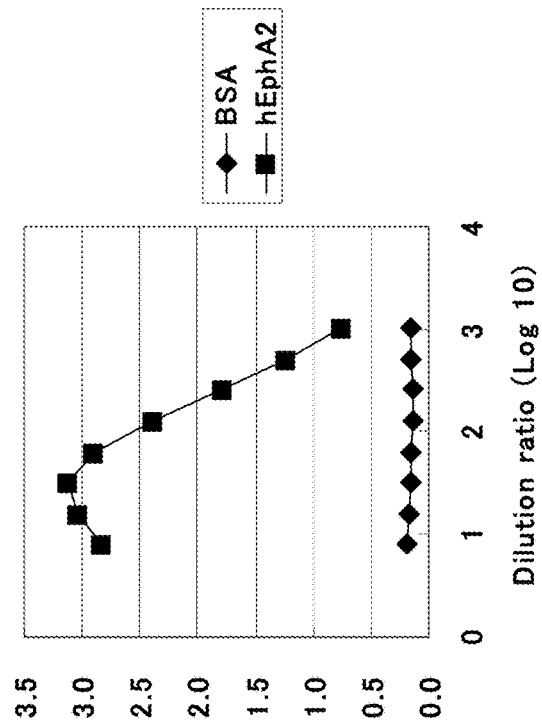
FIG. 1(A) is a diagram showing that a TACI_d2 mutant binds to each protein as a target molecule, wherein the TACI_d2 mutant was obtained by panning against the protein. The target molecule used in the panning is BSA and hEphA2 for FIGS. 1(A)(1) and 1(A)(2), respectively.
FIG. 1(B) is a diagram showing that a TACI_d2 mutant binds to each protein as a target molecule, wherein the TACI_d2 mutant was obtained by panning against the protein. The target molecule used in the panning is hEGFR/Fc and hErbB2/Fc for FIGS. 1(B)(3) and 1(B)(4), respectively.
FIG. 1(C) is a diagram showing that a TACI_d2 mutant binds to each protein as a target molecule, wherein the TACI_d2 mutant was obtained by panning against the protein. The target molecule used in the panning is hVEGF, and hTNF-α for FIGS. 1(C)(5) and 1(C)(6), respectively.
Figure 1:
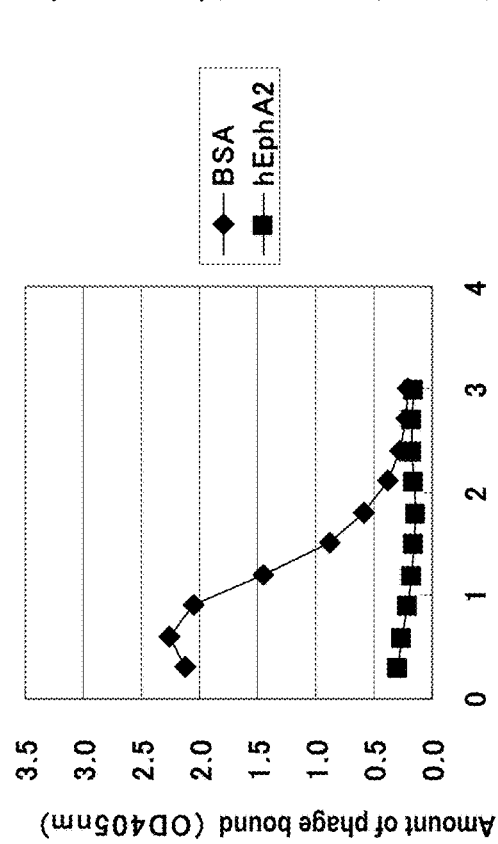
Figure 1:
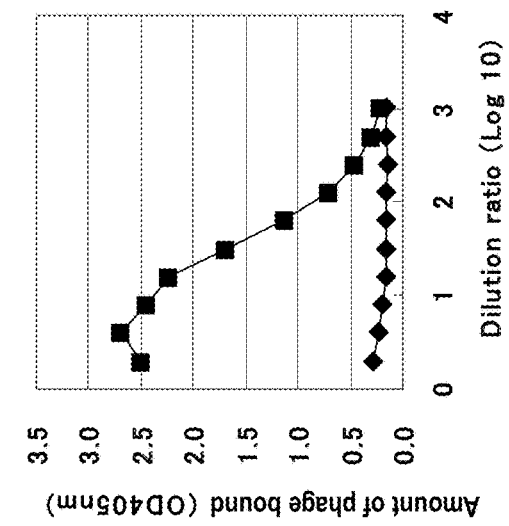
Figure 1:
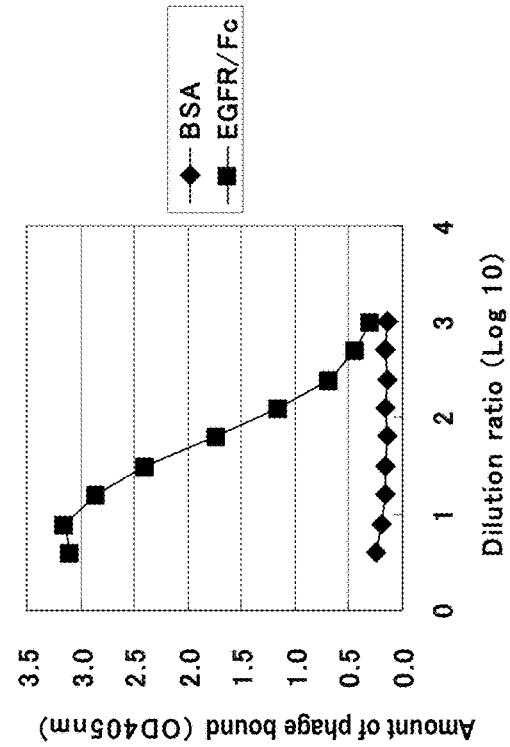
Figure 1:
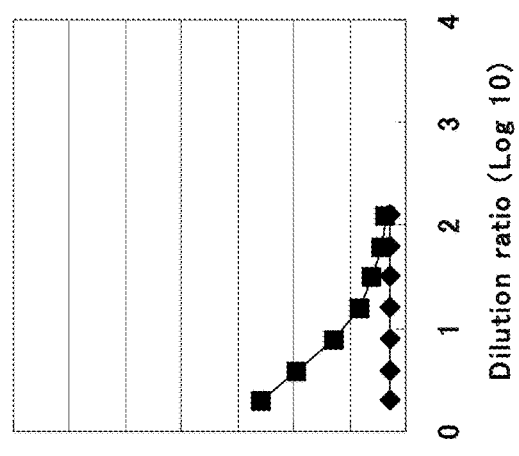
Figure 1:
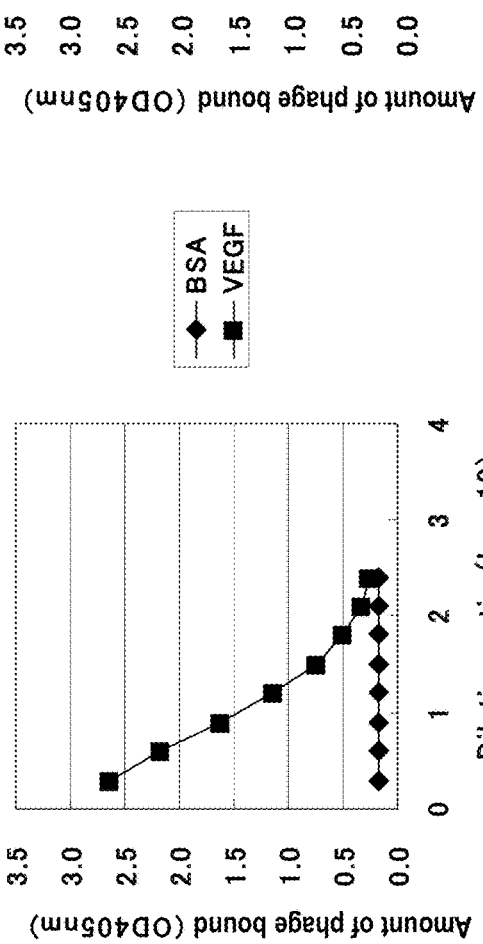

The present invention provides a peptide, a derivative of the peptide, a peptide library, a nucleic acid, a vector, a cell, a method for producing the peptide and/or the derivative thereof, a method for identifying a peptide and/or a derivative thereof having desired properties, a method for producing a peptide and/or derivative thereof having desired properties, a method for determining whether or not a test peptide or test derivative thereof binds to a target molecule, a nucleic acid library, a composition, a reagent, etc. Hereinafter, various aspects of the present invention will be described. However, the aspects of the present invention are not limited thereto.

1. Peptide

The present invention provides a peptide.

The "peptide" of the present invention even incorporates a "polypeptide" and a "protein" in its meaning. In the present invention, this "peptide" even incorporates a "peptide derivative" in its meaning.

According to one aspect of the present invention, the peptide has the amino acid sequence represented by SEQ ID NO: 1 in the Sequence Listing. In the amino acid sequence, each of the 1st Xaa to the 11th Xaa counting from the amino terminus is any amino acid, preferably any amino acid other than cysteine, more preferably any amino acid other than cysteine and proline.

According to an even more preferred aspect of the present invention, in the amino acid sequence of the peptide, the 1st Xaa counting from the amino terminus (corresponding to an amino acid at position 11 in SEQ ID NO: 1) is an amino acid selected from the group consisting of glutamine, methionine, histidine, serine, glutamic acid, asparagine, tryptophan, isoleucine, aspartic acid, and threonine; the 2nd Xaa counting from the amino terminus (corresponding to an amino acid at position 13 in SEQ ID NO: 1) is an amino acid selected from the group consisting of tryptophan, leucine, glycine, isoleucine, methionine, aspartic acid, asparagine, and threonine; the 3rd Xaa counting from the amino terminus (corresponding to an amino acid at position 14 in SEQ ID NO: 1) is an amino acid selected from the group consisting of arginine, leucine, alanine, histidine, threonine, valine, glutamic acid, and serine; the 4th Xaa counting from the amino terminus (corresponding to an amino acid at position 15 in SEQ ID NO: 1) is an amino acid selected from the group consisting of glutamic acid, arginine, lysine, isoleucine, glutamine, tryptophan, tyrosine, glycine, and phenylalanine; the 5th Xaa counting from the amino terminus (corresponding to an amino acid at position 16 in SEQ ID NO: 1) is an amino acid selected from the group consisting of lysine, glutamic acid, methionine, alanine, glutamic acid, glycine, threonine, histidine, and tryptophan; the 6th Xaa counting from the amino terminus (corresponding to an amino acid at position 17 in SEQ ID NO: 1) is an amino acid selected from the group consisting of tryptophan, tyrosine, serine, phenylalanine, glutamine, and aspartic acid; the 7th Xaa counting from the amino terminus (corresponding to an amino acid at position 20 in SEQ ID NO: 1) is an amino acid selected from the group consisting of glutamic acid, aspartic acid, alanine, serine, lysine, arginine, histidine, and asparagine; the 8th Xaa counting from the amino terminus (corresponding to an amino acid at position 25 in SEQ ID NO: 1) is an amino acid selected from the group consisting of lysine, glutamic acid, alanine, tyrosine, tryptophan, methionine, leucine, arginine, and glycine; the 9th Xaa counting from the amino terminus (corresponding to an amino acid at position 28 in SEQ ID NO: 1) is an amino acid selected from the group consisting of asparagine, serine, tyrosine, glutamic acid, alanine, glycine, lysine, and histidine; the 10th Xaa counting from the amino terminus (corresponding to an amino acid at position 31 in SEQ ID NO: 1) is an amino acid selected from the group consisting of aspartic acid, histidine, tryptophan, phenylalanine, asparagine, valine, and leucine; and the 11th Xaa counting from the amino terminus (corresponding to an amino acid at position 32 in SEQ ID NO: 1) is an amino acid selected from the group consisting of isoleucine, tyrosine, histidine, glutamic acid, aspartic acid, leucine, alanine, methionine, phenylalanine, and valine. Alternatively, each of the 1st Xaa to the 11th Xaa counting from the amino terminus may be an amino acid varied by conservative amino acid substitution (which is described in detail in the other part of the present invention) from an amino acid selected from each group described in this paragraph.

According to an aspect of the present invention, the peptide has an amino acid sequence derived from the amino acid sequence represented by SEQ ID NO: 1 in the Sequence Listing by the substitution, deletion, addition, or insertion of amino acid(s) except at the 1st Xaa to the 11th Xaa counting from the amino terminus. The number of substituted, deleted, added, or inserted amino acid(s) in the amino acid sequence represented by SEQ ID NO: 1 in the Sequence Listing, except at the 1st Xaa to the 11th Xaa counting from the amino terminus, can be 1 to 28 (inclusive). The lower limit thereof is 1. The upper limit thereof is 28, 26, 24, 22, 20, 18, 16, 14, 12, 10, 8, 6, 5, 4, 3, or 2. 1 is the minimum limit thereof.

In the amino acid sequence, each of the 1st Xaa to the 11th Xaa counting from the amino terminus is any amino acid, preferably any amino acid other than cysteine, more preferably any amino acid other than cysteine and proline, even more preferably an amino acid selected from each group described above or an amino acid varied from the amino acid by conservative amino acid substitution.

A "conservative amino acid substitution" means the substitution of a certain amino acid by an amino acid functionally equivalent or similar thereto. The conservative amino acid substitution in the peptide brings about static change to the amino acid sequence of the peptide. For example, one or more amino acids similar in polarity to amino acid(s) in the peptide act functionally equivalently thereto and bring about static change to the amino acid sequence of this peptide. In general, substitution within a certain group can be regarded as being conservative in terms of structure and function. As is obvious to those skilled in the art, however, the role of a particular amino acid residue may have an implication on the three-dimensional structure of a molecule containing the amino acid. For example, a cysteine residue can take an oxidized (disulfide) form having lower polarity than that of a reduced (thiol) form. A long aliphatic moiety in an arginine side chain can constitute structurally and functionally important features. Also, an aromatic ring-containing side chain (tryptophan, tyrosine, and phenylalanine) can contribute to ion-aromatic interactions or cation-pi interactions. In this case, the substitution of an amino acid having such a side chain by an amino acid belonging to an acidic or nonpolar group can be structurally and functionally conservative. Residues such as proline, glycine, and cysteine (disulfide form) may have a direct impact on the three-dimensional structure of the main chain and can hardly be substituted without structural distortion.

A conservative amino acid substitution includes, as shown below, specific substitution based on side chain similarity (L. Lehninger, Biochemistry, 2nd edition, pp 73-75, Worth Publisher, New York (1975)) and typical substitution.

(1) Nonpolar amino acid group: alanine (hereinafter, referred to as "Ala" or simply as "A"), valine (hereinafter, referred to as "Val" or simply as "V"), leucine (hereinafter, referred to as "Leu" or simply as "L"), isoleucine (hereinafter, referred to as "Ile" or simply as "I"), proline (hereinafter, referred to as "Pro" or simply as "P"), phenylalanine (hereinafter, referred to as "Phe" or simply as "F"), tryptophan (hereinafter, referred to as "Trp" or simply as "W"), and methionine (hereinafter, referred to as "Met" or simply as "M")

(2) Uncharged polar amino acid group: glycine (hereinafter, referred to as "Gly" or simply as "G"), serine (hereinafter, referred to as "Ser" or simply as "S"), threonine (hereinafter, referred to as "Thr" or simply as "T"), cysteine (hereinafter, referred to as "Cys" or simply as "C"), tyrosine (hereinafter, referred to as "Tyr" or simply as "Y"), asparagine (hereinafter, referred to as "Asn" or simply as "N"), and glutamine (hereinafter, referred to as "Gln" or simply as "Q")

(3) Acidic amino acid group: aspartic acid (hereinafter, referred to as "Asp" or simply as "D") and glutamic acid (hereinafter, referred to as "Glu" or simply as "E")

(4) Basic amino acid group: lysine (hereinafter, referred to as "Lys" or simply as "K"), arginine (hereinafter, referred to as "Arg" or simply as "R"), and histidine (hereinafter, referred to as "His" or simply as "H")

Naturally occurring amino acids can be divided into the following groups based on the properties of their common side chains:

(1) Hydrophobic amino acid group: norleucine, Met, Ala, Val, Leu, and Ile
(2) Neutral hydrophilic amino acid group: Cys, Ser, Thr, Asn, and Gln
(3) Acidic amino acid group: Asp and Glu
(4) Basic amino acid group: His, Lys, and Arg
(5) Group of amino acids influencing the direction of the main chain: Gly and Pro
(6) Aromatic amino acid group: Trp, Tyr, and Phe Hereinafter, examples of the conservative substitution will be shown. However, the conservative amino acid substitution of the present invention is not limited thereto.

Ala may be substituted by, for example, Val, Leu, Ile, Met, norleucine, Pro, Phe, or Trp.

Arg may be substituted by, for example, Lys or His.

Asn may be substituted by, for example, Cys, Ser, Thr, Gln, Tyr, or Gly.

Asp may be substituted by, for example, Glu.

Cys may be substituted by, for example, Gly, Ser, Thr, Tyr, Asn, or Gln.

Gln may be substituted by, for example, Gly, Ser, Thr, Cys, Tyr, or Asn.

Glu may be substituted by, for example, Asp.

Gly may be substituted by, for example, Ser, Cys, Thr, Tyr, Asn, Gln, Pro, Asp, or Glu.

His may be substituted by, for example, Lys or Arg.

Ile may be substituted by, for example, Leu, Val, Met, Pro, Ala, Phe, Trp, or norleucine.

Leu may be substituted by, for example, norleucine, Ile, Val, Pro, Met, Ala, Phe, Trp, or Met.

Lys may be substituted by, for example, Arg or His.

Met may be substituted by, for example, Ala, Val, Leu, Phe, Ile, Pro, Trp, or norleucine.

Norleucine may be substituted by, for example, Met, Ala, Val, Leu, Ile, Pro, Phe, or Trp.

Phe may be substituted by, for example, Trp, Leu, Val, Ile, Ala, Tyr, Pro, or Met.

Pro may be substituted by, for example, Ala, Val, Leu, Ile, Phe, Trp, Met, or Gly.

Ser may be substituted by, for example, Thr, Cys, Asn, Gln, Gly, or Tyr.

Thr may be substituted by, for example, Val, Ser, Gly, Cys, Tyr, Asn, or Gln.

Trp may be substituted by, for example, Tyr, Phe, Ala, Val, Leu, Ile, Pro, or Met.

Tyr may be substituted by, for example, Gly, Cys, Asn, Gln, Trp, Phe, Thr, or Ser.

Val may be substituted by, for example, Ile, Leu, Met, Trp, Phe, Ala, norleucine, or Pro.

Examples of the amino acid sequence of the peptide of the present invention having the amino acid sequence constituted of these amino acids can include the following, though the amino acid sequence of the peptide of the present invention is not limited thereto:

```
SLSCRKEQGKQYWREKMDCECASKCGNHPDICAYFCEN
(SEQ ID NO: 2 in the Sequence Listing: No. 1
in FIG. 4)

SLSCRKEQGKQYLLREWDCDSCASECGSHPHYCAYFCEN
(SEQ ID NO: 3 in the Sequence Listing: No. 2
in FIG. 4)

SLSCRKEQGKMYLLKEWDCASCASACGNHPHYCAYFCEN
(SEQ ID NO: 4 in the Sequence Listing: No. 3
in FIG. 4)

SLSCRKEQGKHYLLKEYDCDSCASECGYHPDYCAYFCEN
(SEQ ID NO: 5 in the Sequence Listing: No. 4
in FIG. 4)

SLSCRKEQGKSYGAIMYDCSSCASYCGEHPWHCAYFCEN
(SEQ ID NO: 6 in the Sequence Listing: No. 5
in FIG. 4)

SLSCRKEQGKEYGAIAWDCSSCASYCGAHPFECAYFCEN
(SEQ ID NO: 7 in the Sequence Listing: No. 6
in FIG. 4)

SLSCRKEQGKNYIHQQWDCASCASECGGHPNYCAYFCEN
(SEQ ID NO: 8 in the Sequence Listing: No. 7
in FIG. 4)

SLSCRKEQGKWYMTWESDCKSCASWCGSHPFDCAYFCEN
(SEQ ID NO: 9 in the Sequence Listing: No. 8
in FIG. 4)

SLSCRKEQGKMYDLYGFDCRSCASMCGKHPDLCAYFCEN
(SEQ ID NO: 10 in the Sequence Listing: No. 9
in FIG. 4)

SLSCRKEQGKMYMVWTQDCKSCASWCGAHPVACAYFCEN
(SEQ ID NO: 11 in the Sequence Listing: No. 10
in FIG. 4)

SLSCRKEQGKIYNQYGFDCKSCASWCGKHPDMCAYFCEN
(SEQ ID NO: 12 in the Sequence Listing: No. 11
in FIG. 4)

SLSCRKEQGKIYMTWHDDCHSCASLCGSHPLFCAYFCEN
(SEQ ID NO: 13 in the Sequence Listing: No. 12
in FIG. 4)

SLSCRKEQGKDYMVFGQDCHSCASWCGKHPVACAYFCEN
(SEQ ID NO: 14 in the Sequence Listing: No. 13
in FIG. 4)

SLSCRKEQGKQYMAGHFDCNSCASRYGHHPLMCAYFCEN
(SEQ ID NO: 15 in the Sequence Listing: No. 14
in FIG. 4)

SLSCRKEQDKTYIEYGFDCRSCASGCGGHPLMCAYFCEN
(SEQ ID NO: 16 in the Sequence Listing: No. 15
in FIG. 4)

SLSCRKEQGKSYTSEWFDCASCASKYGKHPLVCAYFCEN
(SEQ ID NO: 17 in the Sequence Listing: No. 16
in FIG. 4)
```

In the present invention, the amino acid can be L-amino acid, D-amino acid, or a mixture thereof (DL-amino acid) but means L-amino acid unless otherwise specified.

In the present invention, an amino acid may be any of amino acids other than those described above (hereinafter, these amino acids are collectively referred to as "abnormal amino acids" for the sake of convenience). Examples of abnormal amino acids can include selenocysteine, N-formylmethionine, pyrrolysine, pyroglutamic acid, cystine, hydroxyproline, hydroxylysine, thyroxine, O-phosphoserine, desmosine, β-alanine, sarcosine, ornithine, creatine, γ-aminobutyric acid, opine, theanine, tricholomic acid, kainic acid, domoic acid, and acromelic acid, which are found in natural peptides or proteins. Examples of non-natural amino acids can include, but not limited to: N-terminally protected amino acids such as Ac-amino acid, Boc-amino acid, Fmoc-amino acid, Trt-amino acid, and Z-amino acid; C-terminally protected amino acids such as t-butyl ester, benzyl ester, cyclohexyl ester, and fluorenyl ester of amino acids; and other amino acids including diamine, ω amino acid, β amino acid, γ amino acid, Tic derivatives of amino acids, and aminophosphonic acid.

The peptide of the present invention can be prepared by a method for producing peptides or proteins, well known to those skilled in the art, such as chemical synthesis, gene recombination, or in vitro translation. Also, the peptide from the library of the present invention or the like screened for by the identification method of the present invention can be prepared by such a method.

Examples of the chemical synthesis method can include, but are not limited to, a t-butoxycarbonyl (Boc) method and a 9-fluorenylmethoxycarbonyl (Fmoc) method. The Fmoc method has advantages such as mild deprotection conditions and the convenient excision of peptides from resins (Fmoc solid phase peptide synthesis: a practical approach, ed. by W. C. Chan, P. D. White Eds., Oxford University Press, New York, 2000.).

In the present invention, the "derivative of the peptide" and the "peptide derivative" mean a chemically modified or biologically modified form of the peptide of the present invention. The chemical modification means the conversion of the original peptide into a different substance through a chemical reaction, i.e., the formation or cleavage of an atom-atom bond, in or on the peptide of the present invention. The biological modification means the conversion of the original peptide into a different substance through a biological reaction, i.e., through the use of an organism-derived protein (enzyme, cytokine, etc.), nucleic acid (ribozyme, etc.), cell, tissue, or organ, or a non-human individual or by the direct or indirect action thereof, in or on the peptide of the present invention.

This "derivative" is not particularly limited as long as the derivative is a substance different from the original peptide. Examples thereof can include a substance containing a naturally occurring sugar chain or an artificially developed sugar chain, a substance containing a polymer such as polyethylene glycol (PEG), a substance containing a synthetic compound or a natural compound, a labeled substance, a substance containing a moiety necessary for solid-phase immobilization, a substance containing a signal peptide linked to the amino terminus, a substance containing a tag for use in purification or isolation, and a substance in which a peptide as a phenotype is linked directly or indirectly to a genotype corresponding to the phenotype, and combinations of two or more thereof.

The derivative of the peptide of the present invention can be prepared by subjecting the peptide of the present invention, as a starting material, to a method for chemically or biologically modifying peptides or proteins that is well known to those skilled in the art, such as chemical reaction, biochemical reaction, or post-translational modification. The derivative of a peptide from the library of the present invention or the like, screened for by the identification method of the present invention can also be prepared by such a method. Alternatively, the post-translationally modified peptide derivative of the present invention may be prepared by gene recombination using a cell capable of providing desired post-translational modification. In addition, the peptide derivative of the present invention containing a modified amino acid can be prepared by adding the modified amino acid to an in vitro translation system.

Examples of the PEGylation method can include, but are not limited to, a method involving reacting peptides or proteins with N-hydroxysuccinimide ester (NHS)-PEG.

According to a preferred aspect, the peptide of the present invention and the derivative thereof each bind to a target molecule.

Examples of the form that can be taken by the peptide of the present invention and the derivative thereof can include, butare not limited to, an isolated form (freeze-dried preparation, solution, etc.), a form bound with an additional molecule (solid-phase immobilized form, fusion protein, an assembly with a foreign molecule, form bound with a target molecule, etc.), a physical collection containing even other peptides, etc. (including the peptide library of the present invention), a form expressed or displayed on cell surface (on *Escherichia coli* or yeast cell surface, etc.) (including the cell of the present invention), and a form expressed or displayed on a viral particle. A form suitable for a purpose such as use or storage can be selected freely.

2. Nucleic Acid

The present invention provides a nucleic acid.

In the present invention, the "nucleic acid" is a mononucleotide, an oligonucleotide, or a polynucleotide and is also referred to as a "gene". Examples of the nucleic acid of the present invention can include, but not limited to, DNA, cDNA, RNA, mRNA, cRNA, probes, oligonucleotides, polynucleotides, primers, and vectors. Also, the nucleic acid of the present invention can be any of single-stranded nucleotides, double-stranded nucleotides, and an hybrid of 3 or more nucleotides strands and encompasses even a single-stranded nucleotides hybrid consisting of DNA and RNA, a double-stranded nucleotides consisting of the nucleotide and its complementary strand, a double-stranded hybrid consisting of single-stranded DNA and single-stranded RNA, double-stranded RNA, single-stranded nucleotides that may have a double-stranded structure moiety in its molecule, etc. The nucleic acid of the present invention may further contain one or more (artificially developed) bases or one or more mononucleotides, other than naturally occurring bases or mononucleotides.

Preferred examples of the nucleic acid of the present invention can include a nucleic acid comprising nucleotides consisting of a nucleotide sequence encoding the amino acid sequence of the peptide of the present invention, and a nucleic acid comprising a nucleotide sequence encoding the amino acid sequence of the peptide of the present invention. This preferred nucleic acid may contain a nucleotide sequence other than the nucleotide sequence encoding the amino acid sequence of the peptide of the present invention, and/or a non-nucleotide moiety and may be modified chemically or biologically (which is described in the other part of the present invention). These forms are all encompassed by the "nucleic acid".

The nucleic acid of the present invention also encompasses a nucleic acid consisting of a nucleotide sequence encoding the amino acid sequence of the peptide of the present invention.

In the present invention, in the case where the amino acid sequence of the peptide of the present invention is encoded by a portion or the whole of the nucleotide sequence of certain nucleotides, this nucleic acid is referred to as a "nucleic acid encoding or corresponding to the amino acid sequence of the peptide" and this peptide is referred to as a "peptide encoded by or corresponding to the nucleic acid".

Examples of the nucleic acid encoding the amino acid sequence of the peptide of the present invention can include, but are not limited to, a nucleic acid comprising a nucleic acid consisting of a nucleotide sequence encoding the amino acid sequence of the peptide of the present invention, a nucleic acid comprising a nucleotide sequence encoding the amino acid sequence of the peptide of the present invention, and a nucleic acid consisting of a nucleotide sequence encoding the amino acid sequence of the peptide of the present invention.

Examples of the peptide corresponding to the nucleic acid of the present invention can include, but not limited to, a peptide comprising a peptide consisting of an amino acid sequence encoded by a portion or the whole of the nucleotide sequence of the nucleic acid of the present invention, a peptide comprising an amino acid sequence encoded by a portion or the whole of the nucleotide sequence of the nucleic acid of the present invention, a peptide consisting of an amino acid sequence encoded by a portion or the whole of the nucleotide sequence of the nucleic acid of the present invention, and a derivative of any one of these peptides.

In the present invention, the phrase "genotype corresponding to (the) phenotype" is also used interchangeably with the "nucleic acid encoding the amino acid sequence of the peptide". Likewise, the phrase "phenotype corresponding to (the) genotype" is also used interchangeably with the "peptide encoded by the nucleic acid".

When the chemically or biologically modified form of the nucleic acid of the present invention contains the peptide of the present invention, this modified form is encompassed in the scope of the "derivative of the peptide" of the present invention.

More preferred examples of the nucleic acid of the present invention can include, of the preferred nucleic acid described above, a nucleic acid comprising a nucleic acid consisting of a nucleotide sequence encoding the amino acid sequence of the peptide of the present invention binding to a target molecule, a nucleic acid comprising a nucleotide sequence encoding the amino acid sequence of the peptide of the present invention binding to a target molecule, and a nucleic acid consisting of a nucleotide sequence encoding the amino acid sequence of the peptide of the present invention binding to a target molecule.

In the present invention, one or more codons corresponding to each amino acid can be used for designing the nucleotide sequence encoding the amino acid sequence. Hence, a nucleotide sequence encoding the single amino acid sequence of a certain peptide or protein may have a plurality of variations. For the selection of such codons, the codons can be selected appropriately according to the codon usage of cells (host cells) to harbor a genotype corresponding to the peptide, i.e., a nucleic acid comprising the nucleotide sequence, or the frequency or rate of a plurality of codons used can be adjusted appropriately. For example, in the case of using *Escherichia coli* cells as host cells, the nucleotide sequence can be designed using codons with high frequency in use in *Escherichia coli*.

The nucleic acid of the present invention can be prepared by a method for producing a nucleic acid well known to those skilled in the art, such as chemical synthesis or gene recombination. A nucleic acid encoding the amino acid sequence of the peptide recovered from the library of the present invention or the like (including screened for, enriched, and isolated) by the identification method of the present invention can also be prepared by such a method.

Examples of the form that can be taken by the nucleic acid of the present invention can include, but are not limited to, an isolated form (freeze-dried preparation, solution, etc.), a form bound with an additional molecule (solid-phase immobilized form, etc.), a recombinant vector comprising the nucleic acid (the vector of the present invention), a cell harboring the nucleic acid or the vector (the cell of the present invention), a form contained in a virus or a viral particle (including a form contained as the vector of the present invention), and a physical collection containing even other nucleic acids, etc. (including the nucleic acid library of the present invention). A form suitable for a purpose such as use or storage can be selected freely.

3. Vector

The present invention provides a recombinant vector (hereinafter, also simply referred to as a "vector").

The vector of the present invention is not particularly limited as long as the vector comprises the nucleic acid of the present invention and serves as means for transferring the nucleic acid of the present invention to cells, microorganisms, or individuals. Preferred examples thereof can include nucleic acid vectors such as phagemids, cosmids, and plasmids.

The vector of the present invention may be a virus that infects prokaryotic cells or eukaryotic cells, or a viral vector.

In the present invention, the "phagemid" means a bacterial plasmid containing an origin of plasmid replication as well as the second replication origin derived from a single-stranded bacteriophage. A cell having this phagemid can replicate the phagemid via a single strand replication mode in coinfection with M13 or its analogous helper bacteriophage. Specifically, single-stranded phagemid DNA is packaged in an infective particle coated with a bacteriophage coat protein. In this way, the phagemid DNA can be formed as a cloned double-stranded DNA plasmid in the infected bacterium, while the phagemid can be formed as a bacteriophage-like particle from the culture supernatant of the coinfected cell. In order to infect a bacterium having F-pilus with the DNA, the bacteriophage-like particle can be injected into the bacterium to reform the particle itself as a plasmid.

A fusion gene comprising the nucleic acid encoding the amino acid sequence of the peptide of the present invention and a bacteriophage coat protein gene can be inserted to the phagemid. Bacterial cells can be infected with the resulting phagemid and cultured to express or display the peptide on the bacterium or a phage-like particle or to produce a fusion protein of the peptide and the coat protein into a phage particle or the culture supernatant of the bacterium.

For example, a fusion gene comprising the nucleic acid encoding the amino acid sequence of the peptide of the present invention and a bacteriophage coat protein gene gpIII is inserted to the phagemid. *Escherichia coli* can be coinfected with the resulting phagemid and M13 or its analogous helper phage to produce a fusion protein comprising the peptide and the coat protein into the culture supernatant of the *Escherichia coli*.

Instead of the phagemid, various circular or noncircular vectors, preferably viral vectors, may be used to express or display the peptide encoded by the nucleotide sequence of the nucleic acid of the present invention contained in the vector, on a cell harboring the vector or a virus-like particle or to produce the peptide into the culture supernatant of the cell according to a method well known to those skilled in the art.

The vector (recombinant vector) of the present invention can be prepared by a method well known to those skilled in the art such as gene recombination.

Examples of the form that can be taken by the vector of the present invention can include, but are not limited to, an isolated form (freeze-dried preparation, solution, etc.), a form bound with an additional molecule (solid-phase immobilized form, etc.), a form transferred to a cell (including the recombinant cell of the present invention), and a physical collection containing even other vectors, etc. (including a particular aspect of the nucleic acid library of the present invention). A form suitable for a purpose such as use or storage can be selected freely.

4. Cell

According to one aspect, the present invention provides a recombinant cell (hereinafter, also simply referred to as a "cell").

The cell of the present invention is a cell that contains the nucleic acid encoding the amino acid sequence of the peptide of the present invention and that expresses the peptide. Any of eukaryotic cells (including established cell lines, primary cultured cells, and subcultured cells) and prokaryotic cells can be used as a host cell or cell of the present invention without particular limitations.

Examples of the prokaryotic cells can include, but are not limited to, bacterial cells such as *Escherichia coli* and *Bacillus subtilis* cells.

Examples of the eukaryotic cells can include animal cells, insect cells, yeast cells, and fungal cells. Examples of the animal cells can include, but are not limited to, monkey COS cells (Gluzman, Y., Cell (1981), vol. 23, pp 175-182; American Type Culture Collection No. ATCC CRL-1650), mouse fibroblasts NIH3T3 (American Type Culture Collection No. ATCC CRL-1658), Chinese hamster ovary cells (CHO cells; American Type Culture Collection No. ATCC CCL-61), and dihydrofolate reductase-deficient lines of CHO cells (Urlaub, G. and Chasin, L. A., Proc. Natl. Acad. Sci. USA (1980), vol. 77, pp 4126-4220).

The cell of the present invention can be prepared by transferring the nucleic acid of the present invention or the vector of the present invention to a host cell and can be prepared preferably by transferring the vector of the present invention to a host cell by transfection, transformation, transduction, or the like.

Examples of the vector suitable for the preparation of the cell of the present invention can include, but are not limited to, replicons derived from a species compatible with the prokaryotic cell, i.e., plasmids, cosmids, and phagemids containing a replication origin and one or more nucleotide sequences selected from a regulatory sequence, transcription initiation site, start codon and stop codon (of translation), etc. The nucleic acid or the vector may further contain a nucleotide sequence that can confer phenotypic character (phenotype) selectivity to the cell harboring the vector or the nucleic acid. Such a vector or nucleic acid is transferred to a host cell, and the obtained cell can be cultured to express the peptide of the present invention.

A host cell suitable for the post-translational modification of the peptide of the present invention may be used as the cell of the present invention. The cell of the present invention can be used in (an aspect of) the method for preparing the peptide derivative of the present invention.

Examples of the form that can be taken by the cell of the present invention can include, but are not limited to, an isolated form (frozen preparation, freeze-dried preparation, solution, etc.), a form bound with an additional molecule (solid-phase immobilized form, etc.), a cell harboring the nucleic acid or the vector of the present invention (which is included in the cell of the present invention), a cell expressing or displaying the peptide of the present invention on its surface (which is included in the cell of the present invention), and a physical collection containing even other cells, etc. (including a particular aspect of the nucleic acid library and the peptide library of the present invention). A form suitable for a purpose such as use or storage can be selected freely.

5. Method for Producing Peptide

According to an alternative aspect, the present invention also provides a method for producing the peptide of the present invention.

The peptide of the present invention can be prepared, as mentioned above, by a method for producing peptides or proteins well known to those skilled in the art, such as chemical synthesis, gene recombination, or in vitro translation. A peptide recovered from the library of the present invention or the like (including screened for, enriched, and isolated) by the identification method of the present invention can also be prepared by such a method.

According to an aspect of the present invention, the method for producing the peptide of the present invention comprises the following steps (1-1) and (1-2):
(1-1) culturing a cell (the cell of the present invention) that contains the nucleic acid encoding the amino acid sequence of the peptide of the present invention and that expresses the peptide or the like; and
(1-2) recovering the peptide from the culture.

According to an alternative aspect, the method for producing the peptide of the present invention comprises the following steps (2-1) and (2-2):
(2-1) determining the amino acid sequence of the peptide of the present invention that binds to a target molecule; and
(2-2) preparing a peptide consisting of the amino acid sequence by chemical synthesis or gene recombination.

According to a further alternative aspect, the method for producing the peptide of the present invention comprises the following steps (3-1) and (3-2):

(3-1) preparing mRNA corresponding to the peptide of the present invention; and
(3-2) preparing the peptide by in vitro translation with the mRNA obtained in step (3-1) as a template.

Also, each of these production methods can be combined appropriately with the identification method of the present invention as a preliminary step. Specifically, first, steps included in the identification method of the present invention are carried out, and subsequently, steps included in the production method of the present invention can be carried out. The method for producing the peptide of the present invention may encompass such a method further comprising (each step of) the identification method of the present invention.

Such a method for producing the peptide of the present invention comprises, for example, the following steps (4-1) to (4-3):
(4-1) contacting peptides contained in the peptide library of the present invention with a target molecule;
(4-2) recovering a peptide binding to the target molecule; and
(4-3) preparing the recovered peptide by chemical synthesis, gene recombination, or in vitro translation.

Likewise, each of these production methods can be combined appropriately with the determination method of the present invention as a preliminary step. Specifically, first, steps included in the determination method of the present invention are carried out, and subsequently, steps included in the production method of the present invention can be carried out. The method for producing the peptide of the present invention or the like may encompass such a method further comprising (each step of) the determination method of the present invention.

Such a method for producing the peptide of the present invention or the like comprises, for example, the following steps (5-1) to (5-3):
(5-1) contacting test peptides of the present invention with a target molecule;
(5-2) determining that the test peptide is positive for binding when the test peptide binds to the target molecule, and
(5-3) when the test peptide has been determined to be positive in step (5-2), preparing the peptide by chemical synthesis, gene recombination, or in vitro translation.

The present invention also provides a method for producing the derivative of the peptide (peptide derivative) of the present invention. The peptide derivative of the present invention can be prepared by the method described above (method for producing the peptide) and then subjecting the prepared peptide to chemical reaction, biochemical reaction, post-translational modification, or the like.

Examples of the method for producing the peptide derivative of the present invention can include, but are not limited to, a method comprising each of the steps (1-1) and (1-2), (2-1) and (2-2), (3-1) and (3-2), (4-1) to (4-3), or (5-1) to (5-3), or the like and may further comprise the step of preparing the peptide derivative of the present invention using the peptide of the present invention as a starting material (hereinafter, referred to as a "derivative preparation step").

Alternatively, a cell capable of providing desired post-translational modification may be used in the method for producing the peptide of the present invention to prepare the peptide derivative of the present invention as a peptide provided with the desired post-translational modification. In this case, for example, the cell capable of providing desired post-translational modification can be used as the cell in the steps (1-1) and (1-2) or as a cell (or host cell) applied to the gene recombination in the steps (2-2), (4-3) and (5-3) to prepare the peptide derivative provided with the desired post-translational modification, though the method for preparing the post-translationally modified form of the peptide (as an aspect of the method for producing the peptide derivative) of the present invention is not limited thereto.

6. Library

The present invention provides a library.

In the present invention, the "library" means a physical collection of molecules that are analogous, but not identical, to one another. The molecules contained in this collection can coexist, for example, in one container or may be present in a physically isolated manner as groups or individual molecules in different containers or at different sites on a solid-phase support. A plurality of libraries may be contained in one collection.

The library of the present invention is not limited by any means as long as the library is a physical collection containing non-identical peptides and/or nucleic acids of the present invention. Examples thereof can include a phage display library, a ribosome display library, and a nucleic acid display library.

The "phage display" means a technique (method and means therefor) of linking foreign peptides or proteins to the coat proteins of filamentous phages or the like and expressing or displaying the resulting fusion proteins on phage-like particles. Also, the recovery (including screening, enrichment, and isolation) of nucleic acids corresponding to the peptides or proteins using this technique is encompassed in the scope of the "phage display". The phage display library is one aspect of the library of the present invention used in this technique.

The "ribosome display" means a technique (method and means therefor) of expressing or displaying peptides or proteins in the form of complexes comprising three molecules (mRNA-ribosome-peptide or protein), which are formed during the translation reaction of in vitro translation. In this context, the peptides or proteins are translation products of the mRNAs. Also, the recovery (including screening, enrichment, and isolation) of nucleic acids corresponding to the peptides or proteins using this technique is encompassed in the scope of the "ribosome display". The ribosome display library is an alternative aspect of the library of the present invention used in this technique.

The "nucleic acid display" means a technique (method and means therefor) of expressing or displaying peptides or proteins in the form of complexes comprising a nucleic acid (synonymous with nucleic acids) and peptides or proteins encoded by the nucleic acid (Keefe, A. D and Szostak, J. W., Nature, vol. 410 (2001), pp 715-718). Also, the recovery (including screening, enrichment, and isolation) of a nucleic acid encoding the amino acid sequence of the peptides or proteins using this technique is encompassed in the scope of the "nucleic acid display". The nucleic acid display library is a further alternative aspect of the library of the present invention used in this technique.

Examples of the nucleic acid display can include, but not limited to, mRNA display (Yamaguchi, J. et al., Nucleic Acids Research, vol. 37, No. 16 e108, pp 1-13 (2009)).

The mRNA display is a technique of displaying peptides or proteins in the form of complexes comprising mRNAs and their translation products peptides or proteins associated via intervening moieties (Keefe, A. D and Szostak, J. W., Nature, vol. 410 (2001), pp 715-718).

In the present invention, a physical collection of cells a physical collection of microorganisms (including viruses, phages, phage-like molecules, particles of any of them, etc.), and a physical collection of naturally occurring or artificially developed vectors (including phagemids, cosmids, plasmids, etc.), which comprise a physical collection containing non-identical peptides and/or nucleic acids of the present invention, as well as a physical collection of fragments thereof and a physical collection of chemically and/or biologically modified forms thereof are also encompassed in the scope of the "library".

In the present invention, as mentioned above, one or more codons corresponding to each amino acid can be used for designing the nucleotide sequence encoding the amino acid sequence. Hence, a nucleotide sequence encoding the single amino acid sequence of a certain peptide or protein may have a plurality of variations. For the selection of such codons, the codons can be selected appropriately according to the codon usage of cells (host cells) to harbor a genotype corresponding to the peptide, i.e., a nucleic acid comprising the nucleotide sequence, or the frequency or rate of a plurality of codons used can be adjusted appropriately. Accordingly, in the nucleic acid library of the present invention, each nucleic acid comprising a nucleotide sequence encoding the single amino acid sequence may have a plurality of variations. Specifically, the nucleic acid library of the present invention may comprise a physical collection containing nucleic acids, each comprising a nucleotide sequence encoding the amino acid sequence of a certain peptide. This physical collection of the nucleic acids encoding the amino acid sequence of the particular peptide may form in itself one nucleotides library.

The library of the present invention contains a plurality of molecules that are analogous, but not identical, to one another. The (number of) types of analogous molecules contained in the library are referred to as the "diversity of (the) library". For example, the diversity of a library consisting of 100 types of analogous molecules is $10^2$. In the present invention, the diversity of the library is not particularly limited and preferably has a higher value.

The diversity of the peptide library for use in the identification method of the present invention and the method for producing the peptide, comprising the steps of the identification method is $1\times10^5$ or higher, $2\times10^5$ or higher, $5\times10^5$ or higher, $1\times10^6$ or higher, $2\times10^6$ or higher, $5\times10^6$ or higher, $1\times10^7$ or higher, $2\times10^7$ or higher, $5\times10^7$ or higher, $1\times10^8$ or higher, $2\times10^8$ or higher, $5\times10^8$ or higher, $1\times10^9$ or higher, $2\times10^9$ or higher, $5\times10^9$ or higher, $1\times10^{10}$ or higher, $2\times10^{10}$ or higher, $5\times10^{10}$ or higher, $1\times10^{11}$ or higher, $2\times10^{11}$ or higher, $5\times10^{11}$ or higher, $1\times10^{12}$ or higher, $2\times10^{12}$ or higher, $5\times10^{12}$ or higher, $1\times10^{13}$ or higher, $2\times10^{13}$ or higher, $5\times10^{13}$ or higher, $1\times10^{14}$ or higher, $2\times10^{14}$ or higher, $5\times10^{14}$ or higher, $1\times10^{15}$ or higher, $2\times10^{15}$ or higher, $5\times10^{15}$ or higher, $1\times10^{16}$ or higher, $2\times10^{16}$ or higher, $5\times10^{16}$ or higher, or $1\times10^{17}$ or higher. Such diversity of the library is not limited to an actual measured value and may be a theoretical value.

7. Identification Method

The present invention provides a method for identifying a peptide and/or a peptide derivative binding to a target molecule.

(1) Target Molecule

In the present invention, the "target molecule" means a substance to which the peptide of the present invention binds and also means an endogenous substance present in a human or nonhuman animal individual or an exogenous substance incorporated in vivo into the individual. The target molecule of the present invention is preferably any of endogenous or exogenous enzymes, receptors, ligands of the receptors, humoral factors (e.g., cytokines), other biopolymers, signal transducers, cells, pathogens, toxins, and substances derived from any one or more thereof, for example, fragments, decomposition products, metabolites, or processed products thereof, which can be involved in directly or indirectly in the onset or exacerbation of a disease that may affect the individual, or exhibits correlation or inverse correlation with the disease. Alternatively, the target molecule of the present invention may be any of non-natural substances such as minerals, polymers, plastics, and synthetic low-molecular-weight compounds.

The target molecule of the present invention is used for screening for a peptide from the peptide library of the present invention that binds to the target molecule. The target molecule may be a full-length molecule or a fragment thereof, or a derivative thereof, with any amino acid, peptide, protein, sugar chain, polymer, carrier, or the like added thereto. Alternatively, the target molecule may be solid-phase immobilized.

(2) Preparation of Target Molecule

The target molecule of the present invention can be isolated and/or purified, for use, from a tissue or a cell affected with a disease. Also, the target molecule of the present invention can be prepared by a method for producing peptides or proteins well known to those skilled in the art, such as chemical synthesis, gene recombination, or in vitro translation. From the target molecule thus obtained, the derivative as mentioned above may be prepared, if necessary.

In the present invention, the target peptide or protein can be prepared by, for example: in vitro translation, i.e., a method involving incubating a nucleic acid (such as DNA or cDNA) corresponding to this peptide or protein or a vector containing the nucleic acid in a solution containing an enzyme, a substrate, an energetic material, etc., necessary for transcription and translation to synthesize the desired peptide or protein in vitro; gene recombination, i.e., a method involving transferring the nucleic acid or the vector to prokaryotic or eukaryotic cells (host cells), culturing the obtained recombinant cells, and then recovering the desired peptide or protein from the culture; or chemical synthesis.

In the case where the target molecule is a protein present or a domain thereof on a cell membrane, the molecule can also be prepared as a secreted protein by expressing, in an appropriate host-vector system, a fusion protein comprising the extracellular region of this protein or domain linked to an immunoglobulin (Ig) constant region.

The nucleic acid corresponding to the target molecule can be obtained by, for example, an expression cloning method, though the obtainment method is not limited thereto. The expression cloning method involves constructing an expression library of cDNAs comprising nucleotide sequences encoding the amino acid sequences of peptides or proteins, and performing polymerase chain reaction (hereinafter, referred to as "PCR"; Saiki, R. K., et al., Science (1988), vol. 239, pp 487-489) with this cDNA library as a template using primers specifically amplifying the full length or partial length of the cDNAs to clone cDNAs corresponding to the peptides or proteins.

Examples of kits or reagents applicable to the in vitro translation can include Rapid Translation System (RTS) manufactured by Roche Diagnostics K.K.

Prokaryotic or eukaryotic cells applicable as host cells for preparing the cell of the present invention can be selected appropriately as the host cells for gene recombination.

The recombinant cell (cell harboring the nucleic acid or the vector) obtained by gene recombination can be cultured according to a method well known to those skilled in the art and can be allowed to produce the desired peptide or protein into the culture or into the cell.

The medium for use in this culture can be selected appropriately from among those routinely used according to the host cells. In the case of using *Escherichia coli* cells as host cells, for example, an LB medium can be supplemented, if necessary, with an antibiotic (e.g., ampicillin) and IPTG and subjected to the culture.

The desired peptide or protein produced intracellularly or extracellularly from the recombinant cell by this culture can be purified and isolated by the appropriate combination of fractionation approaches known in the art using, for example, its physical, chemical, and/or biological properties.

Examples of the fractionation approaches can include, but are not limited to, salting out, treatment with a protein precipitant, dialysis, ultrafiltration, molecular sieve (gel filtration) chromatography, adsorption chromatography, ion-exchange chromatography, affinity chromatography, partition chromatography, and hydrophobic chromatography.

Alternatively, a moiety useful for purification may be linked or added to the peptide or protein in advance. As a result, the desired peptide or protein can be purified efficiently. For example, a histidine tag consisting of 6 residues can be linked to the peptide or protein in advance to efficiently purify the desired peptide or protein by nickel affinity chromatography. Alternatively, an IgG Fc region can be liked thereto in advance to efficiently purify the desired peptide or protein by protein A affinity chromatography.

(3) Contact of Peptide and/or Peptide Derivative with Target Molecule

The identification method of the present invention comprises the step of contacting peptides and/or derivatives thereof with the target molecule. In this context, the peptides and/or the derivatives thereof may be contained in the peptide library. Specifically, the identification method of the present invention may comprise the step of contacting peptides and/or derivatives thereof contained in the peptide library with the target molecule.

In the present invention, the term "contacting" means that two or more substances are brought into proximity so that two or more of these substances can be interacted with each other. Examples of the interaction can include, but not limited to: covalent bonds, coordinate bonds, metal-metal bonds, ionic bonds, metallic bonds, hydrogen bonds, and Van der Waals bond (hereinafter, these bonds are referred to as "chemical bonds"); interactions based on electrostatic interactions such as bonds based on Coulomb force, interionic interactions, hydrogen bonds, dipolar interactions, and Van der Waals force (hereinafter, these interactions are referred to as "intermolecular force"); and other interactions, charge-transfer interactions, transannular interactions, hydrophobic interactions, and association of peptides and biomolecules. In the present invention, the "two or more substances" are not particularly limited as long as the substances include the target molecule and a test substance. The test substance is not particularly limited as long as the substance binds to the target molecule. Examples thereof can include the peptide of the present invention, the derivative of the peptide, a solid-phase carrier with the peptide or the peptide derivative immobilized thereon, and a cell, a viral particle, or a virus-like particle (including phages and phagemids) expressing or displaying the peptide or the peptide derivative. This test substance may be expressed or displayed on the surface of a eukaryotic or prokaryotic cell, on a viral particle or a virus-like particle, or in a ribosomeor nucleic acid-linked form by phage display, ribosome display, nucleic acid display, or the like.

(4) Screening

The identification method of the present invention comprises the step of screening for a peptide and/or a peptide derivative having desired properties, preferably a peptide and/or a peptide derivative binding to the target molecule.

In the present invention, the terms "binding" or "bound" means that two or more substances are in proximity or in an associated state with each other under a certain condition to the extent that these substances can be interacted (which is described in the other part of the present invention) with each other.

In the present invention, test substances are contacted with target molecules under a certain condition. Subsequently, a test substance nonspecifically adsorbed to the target molecule and a test substance unbound or unadsorbed to the target molecule are removed from a test substance-containing fraction. If a test substance is present in the resulting fraction, this test substance can be regarded as "binding" to the target molecule.

When mere nonspecific adsorption occurs between two or more substances, the "binding" can be regarded as not occurring between these substances. In addition, when two or more substances contacted with each other are neither in proximity nor in an associated state with each other to the extent that these substances can be interacted (which is described in the other part of the present invention) with each other, the "binding" can be regarded as not occurring between the substances.

For example, a fluorescence antibody method (direct or indirect method), radioimmunoassay, enzyme immunoassay (homogeneous or heterogeneous method), ELISA, or ELISPOT, which performs assay by flow cytometry or the like is widely used as a method for determining the "binding" between an antibody and an antigen. In these methods, the presence or absence of the "binding" between the peptide or the derivative thereof and the target molecule can be determined in the same way as in the determination of the "binding" between an antibody and an antigen except that the test antibody and the antigen are replaced with the peptide of the present invention or the derivative thereof and the target molecule.

Also, the presence or absence of the "binding" can be determined by measuring an index for binding activity or affinity. Examples of the index for binding affinity can include a dissociation constant and an association constant.

Provided that the chemical equilibrium between a molecule A and an A-binding substance B is defined as follows:

the dissociation constant (Kd) of chemical dissociation thereof can be calculated according to the following expression:

$$Kd=[A][B]/[AB]$$

wherein [A], [B], and [AB] represent the concentrations of the molecule A, the substance B, and an assembly AB, respectively; Kd represents the ratio of the molecule A and the substance B dissociated from each other to the undissociated assembly AB; and the reciprocal of Kd represents an association constant (Ka).

The "dissociation constant" used in the present invention means mainly the equilibrium dissociation constant of the peptide and/or the peptide derivative for binding to a certain target molecule.

In the present invention, the dissociation constant can be calculated by measuring the concentrations of dissociated substances (peptide, peptide derivative, target molecule, etc.) and undissociated substances (assembly of the peptide and/or the peptide derivative and the target molecule, etc.). The method for determining and calculating the dissociation constant is not particularly limited as long as the method is well known to those skilled in the art. Examples thereof can include a method using surface plasmon resonance and an isothermal titration calorimetry method.

In the method using surface plasmon resonance, the interaction between the target molecule and the peptide and/or the derivative thereof binding thereto can be determined and calculated as follows: a series of association and dissociation reactions is detected by surface plasmon resonance at a plurality of peptide concentrations; the obtained series of association and dissociation reactions is analyzed; and the dissociation constant is calculated from various rate constants thus obtained.

Examples of the determination-calculation system of surface plasmon resonance can include, but not limited to, Biacore system (GE Healthcare Japan Corp.). Procedures for the method using Biacore system are as follows: target molecules are immobilized onto a sensor chip of Biacore system by amine coupling; the target molecules are contacted with peptides at a plurality of peptide concentrations; the interaction therebetween is detected by surface plasmon resonance; a series of association and dissociation reactions is drawn in a sensorgram with time as the abscissa against the amount of binding (RU) as the ordinate; the sensorgram drawn at the plurality of peptide concentrations is fit to a 1:1 Langmuir model using BIAevaluation software (manufactured by GE Healthcare Japan Corp.) to calculate various rate parameters; and the dissociation constant is calculated from various rate parameters thus calculated.

In the isothermal titration calorimetry method, the interaction between the target molecule and the peptide and/or the derivative thereof binding thereto can be determined and calculated as follows: a peptide solution is added dropwise to a target molecule-containing solution (and vice versa); the quantity of heat generated by the interaction is measured to draw a binding isotherm; and a dissociation constant ($K_D$), stoichiometry of the reaction (N), an enthalpy change ($\Delta H$), and an entropy change ($\Delta S$) are obtained from the binding isotherm.

Examples of the system of directly measuring a very small thermal change (exothermic change or endothermic change) associated with an intermolecular interaction can include, but not limited to, MicroCal system (GE Healthcare Japan Corp.). Procedures for the method using MicroCal system are as follows: a ligand solution is titrated to each sample cell kept at constant temperature, and stirred; heat generation or absorption directly proportional to the amount of binding take places through the intermolecular interaction to change the temperature of the solution in the sample cell; a temperature difference ($\Delta T$) from a reference cell is detected by a cell feedback network (CFB); the reference cell or the sample cell is heated until $\Delta T$ reaches 0; a feedback power required to maintain $\Delta T=0$ is measured to obtain the quantity of heat generated or absorbed through the interaction; the amount of heat generated is plotted as an ordinate against the molar ratio of the peptide to the target molecule as an abscissa, and the dissociation constant is calculated from the binding isotherm.

In the identification method and/or the determination method (which will be described later) of the present invention, a test substance that exhibits a dissociation constant of, for example, 100 µM or smaller, 50 µM or smaller, 20 µM or smaller, 10 µM or smaller, 5 µM or smaller, 2 µM or smaller, 1 µM or smaller, 500 nM (0.5 µM) or smaller, 200 nM or smaller, 100 nM or smaller, 50 nM or smaller, 20 nM or smaller, 10 nM or smaller, 5 nM or smaller, 2 nM or smaller, 1 nM or smaller, 500 pM (0.5 nM) or smaller, 200 pM or smaller, 100 pM or smaller, 50 pM or smaller, 20 pM or smaller, 10 pM or smaller, 5 pM or smaller, 2 pM or smaller, or 1 pM or smaller for the target molecule can be determined to bind to the target molecule, i.e., to be positive, though the reference value of the dissociation constant and the criteria for determining the presence or absence of the "binding" are not limited thereto.

In the identification method of the present invention, the "screening" step also serves as the step of recovering the test substance binding to the target molecule. The product may consist only of the test substance binding to the target molecule or may also contain a substance that does not bind to the target molecule as long as the test substance binding to the target molecule is contained or enriched in the product. The target molecule-binding test substance contained or enriched in this product may be a single substance or may be a mixture of two or more of such substances.

The screening step, i.e., the recovery step, in the identification method of the present invention means the step of recovering a fraction having the target molecule-binding substance contained or enriched therein. This step is not particularly limited as long as the step is performed by a fractionation-purification method well known to those skilled in the technical field of the present invention. The step may comprise, for example, the steps of: separating a substance bound with the target molecule, a substance unbound with the target molecule and a substance nonspecifically adsorbed to the target molecule from the (fraction containing) target molecule; or eluting the substance bound with the target molecule (separating the substance from the target molecule). In this step, the criteria for determining the dissociation constant or the like do not have to be set for the presence or absence of binding.

In the present invention, the "screening" included in the identification method of the present invention is also referred to as "panning". In the present invention, the "panning" means procedures of contacting peptides and/or peptide derivatives of the present invention with the target molecule and recovering (including screening for, concentrating, and isolating) a peptide and/or a peptide derivative binding to the target molecule.

A method well known to those skilled in the art can be applied to the panning. Examples thereof can include, but not limited to, a solid-phase panning method and a liquid-phase panning method. The solid-phase panning method can involve, for example, immobilizing target molecules onto a solid phase, subsequently contacting peptides contained in a liquid phase with the target molecules, subsequently removing a peptide unbound with the target molecule and a nonspecifically bound peptide, and then selectively separating a peptide bound with the target molecule from (the target molecule immobilized on) the solid phase to screen for a peptide having the desired binding activity, though the operation of the solid-phase panning method is not limited thereto. The liquid-phase panning method can involve, for example, contacting peptides with the target molecules in a solution, subsequently removing a peptide unbound with the target molecule and a nonspecifically bound peptide, and then selectively separating a peptide bound with the target molecule from the target to screen for a peptide having the desired binding activity, though the operation of the liquid-phase panning method is not limited thereto.

In the identification method of the present invention, the nucleic acid encoding the amino acid sequence of the peptide (including even the "peptide derivative") binding to the target molecule are efficiently screened for using a library in which a phenotype (synonymous with a phenotypic character) is linked to a genotype (synonymous with a genetic character) corresponding thereto. As a result, the peptide can be prepared efficiently. The link between the phenotype and the genotype corresponding thereto (hereinafter, simply referred to as a "phenotype and a genotype") may be direct or indirect.

The "direct link" between the phenotype and the genotype means that the behaviors of the phenotype and the genotype match with each other. Even if there is a degree of distance between the phenotype and the genotype, for example, due to the presence of an additional intervening moiety, this case is also encompassed in the scope of the "direct link" as long as their behaviors match with each other. Specifically, it is not essential that they should be physically adjacent to each other.

In the present invention, the phrase "behaviors of the phenotype and the genotype match with each other" means that their behaviors match with each other in aspects such as the peptide, the nucleic acid, the vector, the cell, the production method, the identification method, the determination method, the peptide library, the nucleic acid library, the composition, and the reagent of the present invention. In these aspects, even if the "match of the behaviors" is lost wholly or partially due to an internal factor, an external factor, their combination, or any of other factors over time, for the time being, until a certain point in time, or from a certain point in time onward, this case is also encompassed in the scope of the phrase "behaviors match with each other".

Examples of the direct link between the phenotype and the genotype can include a ribosome display library, a nucleic acid display library, a peptide and/or a derivative thereof linked directly or indirectly to the nucleic acid encoding the amino acid sequence of the peptide of the present invention, and a peptide library comprising this peptide and/or derivative thereof.

The "indirect link" between the phenotype and the genotype means that a particular phenotype allows access to a genotype corresponding to the phenotype, though their behaviors do not always match with each other. Examples of the indirect link between the phenotype and the genotype can include, but not limited to, a phage display library and cDNA library for use in expression cloning.

Even though the behavior of the peptide or the derivative thereof as a phenotype does not match with that of the nucleic acid as a genotype corresponding thereto in each clone contained in the phage display library, the peptide and/or the derivative thereof (expressed or displayed on a phage-like particle) binding to the target molecule can be screened for through the steps, for example, of contacting peptides and/or derivatives thereof contained in the library with the target molecule, removing a phage-like particle unbound with the target molecule or nonspecifically adsorbed to the target molecule, and then selectively eluting a phage-like particle bound with the target molecule. In addition, the corresponding genotype, i.e., the nucleic acid encoding the amino acid sequence of this peptide or the peptide derivative thereof can be purified and isolated and further sequenced. The advantages of such access from the phenotype to the genotype corresponding thereto are not limited to the case of the "indirect link" between the phenotype and the genotype in the phage display, etc., and can also be relished in the case of the "direct link" therebetween.

Each step included in the identification method of the present invention can be performed repetitively two or more times. In particular, a new peptide library can be constructed from peptides and/or peptide derivatives recovered in the screening step, and then subjected to the contact and screening steps to enrich, at a higher level, the peptide and/or the derivative thereof binding to the target molecule. This operation can be further repeated to enrich, at a much higher level, the peptide and/or the derivative thereof binding to the target molecule. Finally, the efficiency of isolation thereof can be enhanced. In addition, this higher level of enrichment of the peptide and/or the derivative thereof binding to the target molecule achieves isolation of a binder having higher affinity.

Alternatively, the peptide and/or the derivative thereof binding to the target molecule may be enriched at a higher level by more securely separating the target-bound peptide and/or derivative thereof from a nonspecifically bound one in the step included in the identification method of the present invention. Examples of such a separation method include increase in the number of the step removing a nonspecifically bound peptide, etc., and the change of a reagent (surfactant, etc.) for use in the removal of the nonspecifically bound peptide to a stronger one.

The peptide of the present invention or the derivative thereof can take any form of a monomer, a homo- or hetero-dimer, a trimer, a tetramer, a pentamer, a hexamer, a heptamer, an octamer, and a multimer composed of 9 or more monomers.

The number of the molecule of the peptide of the present invention or the derivative thereof binding to one target molecule or one target site can be any of 1, 2, 3, 4, 5, 6, 7, 8, and 9 or more. This peptide or derivative thereof can bind to the target molecule, in any form of a monomer, a homo- or hetero-dimer, a trimer, a tetramer, a pentamer, a hexamer, a heptamer, an octamer, and a multimer composed of 9 or more monomers.

The number of the target molecule or the target site to which one molecule of the peptide of the present invention or the derivative thereof binds can be any of 1, 2, 3, 4, 5, 6, 7, 8, and 9 or more.

8. Composition

The present invention provides a composition.

The composition of the present invention comprises the peptide, the peptide derivative, the nucleic acid, the vector, or the cell of the present invention.

The composition comprising the peptide of the present invention or the derivative thereof (including those displayed on the surface of the cell of the present invention) can be used for detecting a target molecule to which the peptide or the derivative thereof binds.

The composition comprising the nucleic acid, the vector, or the cell of the present invention can be used for preparing a peptide having an amino acid sequence encoded by the nucleotide sequence of the nucleic acid, or the nucleic acid contained in the vector, or the cell of the present invention. Also, this composition can be used for detecting a nucleic acid, a vector, a cell, etc., containing the nucleic acid.

The composition can comprise, if necessary, for example, a buffer, a salt, a metal, an antiseptic, a surfactant, and a substance for reducing or preventing damage suffered on the peptide, the peptide derivative, the nucleic acid, the vector, or the cell of the present invention by a preparation method such as freezing or freeze drying.

9. Reagent

The present invention provides a reagent.

The reagent of the present invention comprises the peptide, the peptide derivative, the nucleic acid, the vector, or the cell of the present invention.

The reagent comprising the peptide of the present invention or the derivative thereof can be used for detecting a target molecule to which the peptide or the derivative thereof binds.

For example, the amount of HER2 protein present in a tumor tissue is measured by a test called immunohistochemical study (IHC). The test result is assessed in the range of 0 (negative) to 3+ (strongly positive). A tumor patient with an IHC score of 3+ is likely to benefit from treatment with Herceptin, while a tumor patient with an IHC score of 0 or 1+ may be unlikely to benefit from this treatment. A tumor patient with an IHC score of 2+ often undergoes an additional test called fluorescence in situ hybridization (FISH) in order to more accurately determine whether the tumor is HER2-positive. The FISH method measures the number of gene copies and determines a tumor containing a large number of HER2 gene copies to be HER2-positive.

The reagent comprising the nucleic acid, the vector, or the cell of the present invention can be used for detecting a nucleic acid, a vector, a cell, etc., containing the nucleic acid.

The reagent of the present invention may be a composition.

A kit comprising the reagent is also encompassed by the reagent of the present invention.

Also, the peptide or the peptide derivative of the present invention, the cell displaying the peptide or the peptide derivative, etc., can be used as an element recognizing a substance such as a target molecule, in a biosensor for the substance.

10. Determination Method

The present invention provides even a method for determining whether or not a test substance binds to a target molecule.

The determination method of the present invention can employ the same steps as in the steps included in the identification method of the present invention or steps appropriately modified from these steps. The test substance, however, which is subjected to this determination method, does not have to be contained in a collection such as a library. For example, a test peptide or a test peptide derivative subjected to the determination method is not limited to the peptide or the peptide derivative contained in the peptide library and may be a single peptide or peptide derivative separated from other peptides, a mixture containing them, or the like. Specifically, the identification method of the present invention is suitable mainly as a method for screening for one or more having desired properties from the physical collection of test substances, whereas the determination method of the present invention is also suitable as an assay method for examining whether or not a particular test substance has desired properties.

In the determination method of the present invention, for example, determination in the step of determining whether or not the test substance binds to the target molecule can be performed on the basis of whether or not the test substance satisfies conditions regarding an index for affinity such as a dissociation constant. In the screening step, as in the identification method of the present invention, the test substance can be determined to be positive if the test substance is recovered as a substance binding to the target molecule.

EXAMPLES

Hereinafter, the present invention will be described more specifically with reference to Examples. However, the present invention is not limited thereto.

Example 1

Preparation of randomly mutated TACI_d2 phage library

1) Synthesis of Randomly Mutated TACI_d2 Oligonucleotide

The following oligonucleotide (183 bp) was synthesized: 5'-G CTG CAC ACT GTA GGA GAA GAC TGG GCC CAG CCG GCC AGC CTG AGT TGC CGT AAA GAA CAG GGC AAG NNN TAT NNN NNN NNN NNN NNN GAC TGC NNN AGC TGC GCG AGC NNN TGT GGA NNN CAT CCT NNN NNN TGC GCG TAT TTT TGC GAA AAC GCG GCC GCG AGT CCA CGT TCC ATC GGT CA-3' (SEQ ID NO: 18 in the Sequence Listing; "N" in the nucleotide sequence represents any base selected from A, T, G, and C).

The sequence has a 5'-terminal primer-binding region, a restriction enzyme SfiI recognition sequence (SfiI site), a randomly mutated TACI_d2 coding sequence, a NotI site, and a 3'-terminal primer-binding region in this order from its 5' end. Also, the sequences each represented by NNN contain codons encoding 18 amino acids (Ala, Glu, Gln, Asp, Asn, His, Trp, Arg, Lys, Val, Leu, Ile, Phe, Tyr, Ser, Met, Gly, and Thr) other than Cys and Pro, at almost equal probabilities (3.0% to 8.2% for each). As a result, the calculational diversity of randomly mutated TACI_d2 is $6.4 \times 10^{13}$.

2) Preparation of *Escherichia coli* TG-1 Strain Having Randomly Mutated TACI_d2 Phagemid Vector PCR was performed with the oligonucleotides (a total of 2 μg) synthesized in the preceding paragraph 1) as a template using the following two types of primers (synthesized by Sigma Life Science, Sigma-Aldrich Corp.):

```
Primer forward 1:   GCTGCACACTGTAGGAGAAGACTGG
                    (SEQ ID NO: 19 in the Sequence
                    Listing);
and Primer reverse 1:   TGACCGATGGAACGTGGACTC
                    (SEQ ID NO: 20 in the Sequence
                    Listing).
```

The DNA polymerase used was KOD-plus-ver. 2 (manufactured by Toyobo Co., Ltd.). The reaction was performed according to the instructions for 10 cycles under conditions involving an annealing temperature of 64° C. and an elongation temperature of 68° C. The PCR product was digested with restriction enzymes NotI-HF (manufactured by New England Biolabs Inc.) and SfiI (manufactured by New England Biolabs Inc.), and this fragment was used as an insert in ligation described later.

A phagemid vector pCANTAB 5E vector (manufactured by GE Healthcare Japan Corp. (formerly Pharmacia)) was digested with restriction enzymes NotI-HF (manufactured by New England Biolabs Inc.) and SfiI (manufactured by New England Biolabs Inc.). Subsequently, the resulting fragment of the restriction enzyme-digested vector was dephosphorylated using *Escherichia coli*-derived alkaline phosphatase (manufactured by Takara Bio Inc.) and then used as a vector in ligation described later.

The insert and the vector were ligated using T4 DNA ligase (manufactured by New England Biolabs Inc.) (molar ratio between the vector and the insert: 1:3). An *Escherichia coli* TG-1 strain was transformed with this ligation product by electroporation (using BTX Electro Cell Manipulator 600 manufactured by BTX Instrument Division, Harvard Apparatus, Inc.; voltage: 1.98 kV, electric resistance: 186 ohms), then inoculated onto a plate of an LB medium containing 100 μg/mL ampicillin and 1% glucose (hereinafter, referred to as LB/Amp/1% Glu), and cultured at 30° C. for 12 hours to obtain $3.5 \times 10^{10}$ *Escherichia coli* colonies.

3) Large-Scale Preparation of Randomly Mutated TACI_d2 Phage

From the *Escherichia coli* colonies thus obtained in the paragraph 2), an *Escherichia coli* suspension with $OD_{600\ nm}=0.3$ was prepared using a 2×YT medium containing 100 μg/mL ampicillin and 1% glucose (hereinafter, referred to as 2×YT/Amp/1% Glu). The bacterial cells were shake-cultured at 37° C. and allowed to grow until $OD_{600,\ nm}=0.5$. A sufficient amount of HYPERPHAGE M13K07 ΔpIII (manufactured by Progen Biotechnik GmbH) was added thereto to infect the cells at 37° C. for 30 minutes. Subsequently, 100 μg/mL ampicillin, 100 μg/mL kanamycin, and 0.25 mM IPTG (hereinafter, collectively referred to as "2×YT/Amp/Kan/0.25 mM IPTG") were added to the *Escherichia coli*, and the cells were shake-cultured overnight at 22° C. 20% polyethylene glycol 6000 and a 2.5 M NaCl solution (hereinafter, collectively referred to as "20% PEG/2.5 M NaCl solution") were added to the recovered culture supernatant, in ¼ of the amount of the culture supernatant, to precipitate phages. The precipitated phages were suspended in phosphate buffered saline (hereinafter, referred to as "PBS") and used as a randomly mutated TACI-displaying phage library in experiments below.

An *Escherichia coli* TG-1 strain was infected with this phage solution and inoculated to an LB/Amp/1% Glu plate. The number of formed colonies was measured. This phage library had a titer of $1.2 \times 10^{13}$ phages/mL.

Example 2

Screening for TACI_d2 Mutant Binding to Target Molecule

1) Liquid-Phase Panning Method

Each target protein (target molecule) was biotinylated using EZ-Link NHS-Chromogenic Biotin Reagent (manufactured by Thermo Fisher Scientific K.K.) according to the instructions. To this target molecule, a TACI_d2 mutant-displaying phage was added and reacted overnight or for 2 hours. The TACI_d2 mutant-displaying phage used was a randomly mutated TACI_d2-displaying phage library for the 1st round of liquid-phase panning, and phages (randomly mutated TACI_d2-displaying phage library) prepared from *Escherichia coli* colonies obtained in the preceding round, for the 2nd or later rounds. Dynabeads M-280 Streptavidin (manufactured by Invitrogen Corp.; hereinafter, referred to as "Dynabeads") was added to this mixed solution to bind the biotinylated target molecule to the Dynabeads. The Dynabeads were washed with PBS containing 0.05% Tween-20 (hereinafter, referred to as "PBST") a predetermined amount of times. Then, a TACI_d2 mutant-displaying phage bound with the biotinylated target molecule on the surface of the Dynabeads was eluted using 0.1 M glycine-HCl/500 mM NaCl (pH 2.2). The eluted phage was immediately neutralized with 1 M Tris-HCl (pH 8.0) and allowed to infect an *Escherichia coli* TG-1 strain, which was in turn inoculated to an LB/Amp/1% Glu plate and cultured at 30° C. for 12 hours or longer.

2) Solid-Phase Panning Method

Each target protein (target molecule) was added to Nunc Maxisorp flat-bottom 96-well plate (Nunc) (hereinafter, referred to as a Maxisorp plate) and solid-phase immobilized overnight at 4° C. To the Maxisorp plate, TACI_d2 mutant-displaying phages were added and reacted for 2 hours. The TACI_d2 mutant-displaying phages used for the 1st round of solid-phase panning were randomly mutated TACI_d2 mutant-displaying phages, and phages (randomly mutated TACI_d2-displaying phage library) prepared from *Escherichia coli* colonies obtained in the preceding round, were used for the 2nd or later rounds. The Maxisorp plate was washed with PBST a predetermined amount of times. Then, a TACI mutant-displaying phage bound with the target molecule solid-phase immobilized on the Maxisorp plate was eluted using 0.1 M glycine-HCl/500 mM NaCl (pH 2.2). The eluted phage was immediately neutralized with 1 M Tris-HCl (pH 8.0) and allowed to infect an *Escherichia coli* TG-1 strain, which was in turn inoculated to an LB/Amp/1% Glu plate and cultured at 30° C. for 12 hours or longer.

3) Preparation of Phage for Use in Next Round

From the *Escherichia coli* colonies obtained by panning, an *Escherichia coli* suspension with $OD_{600\,nm}$=0.3 for use in a next round was prepared using 2×YT/Amp/1% Glu. The bacterial cells were shake-cultured at 37° C. and allowed to grow until $OD_{600\,nm}$=0.5. A sufficient amount of helper phages M13K07 was added thereto to infect the cells at 37° C. for 30 minutes. After addition of 2×YT/Amp/Kan/0.25 mM IPTG, the helper phage-infected *Escherichia coli* was shake-cultured overnight at 22° C. 20% PEG/2.5 M NaCl solution was added to the recovered culture supernatant to precipitate phages. The precipitated phages were suspended in PBS and were used in the next round of panning.

4) Screening for TACI_d2 Mutant Binding to Target Molecule

Three or four rounds of liquid-phase or solid-phase panning were performed using any one of 6 types of recombinant proteins as a target molecule: IgG-Free, Protease-Free Bovine Serum Albumin (manufactured by Jackson ImmunoResearch Laboratories, Inc.; hereinafter, referred to as "BSA"), Recombinant Human EphA2, CF (manufactured by R&D systems, Inc.; hereinafter, referred to as "hEphA2"), Recombinant Human EGF R/Fc Chimera, CF (manufactured by R&D systems, Inc.; hereinafter, referred to as "hEGFR/Fc"), Recombinant Human ErbB2/Fc Chimera, CF (manufactured by R&D systems, Inc.; hereinafter, referred to as "hErbB2/Fc"), Recombinant Human $VEGF_{165}$ (manufactured by PeproTech, Inc.; hereinafter, referred to as "hVEGF"), and Recombinant Human TNF-α (manufactured by PeproTech, Inc.; hereinafter, referred to as "hTNF-α").

Example 3

Evaluation of Binding Activity of TACI_d2 Mutant(s) Obtained by Panning Against Target Molecule 1) Preparation of Phage for Use in Phage ELISA—(1)

*Escherichia coli* suspension with $OD_{600\,nm}$=0.3 was prepared using 2×YT/Amp/1% Glu from the whole *Escherichia coli* colonies obtained by the final round of panning. The bacterial cells were shake-cultured at 37° C. and allowed to grow until $OD_{600\,nm}$=0.5. A sufficient amount of helper phages M13K07 was added thereto to infect the cells at 37° C. for 30 minutes. After addition of 2×YT/Amp/Kan/0.25 mM IPTG, the helper phage-infected *Escherichia coli* was shake-cultured overnight at 22° C. 20% PEG/2.5 M NaCl solution was added to the recovered culture supernatant to precipitate phages, which were then suspended in PBS. This phage stock solution and a series of two-fold dilutions with PBS were used in phage ELISA.

2) Preparation of Phage for Use in Phage ELISA—(2)

One single colony selected from the *Escherichia coli* colonies obtained by the final round of panning was inoculated to 2×YT/Amp/1% Glu. The bacterial cells were shake-cultured at 37° C. and allowed to grow until $OD_{600\,nm}$=0.5. A sufficient amount of helper phages M13K07 was added thereto to infect the cells at 37° C. for 30 minutes. After addition of 2×YT/Amp/Kan/0.25 mM IPTG, the helper phage-infected *Escherichia coli* was shake-cultured overnight at 22° C. 20% PEG/2.5 M NaCl solution was added to the recovered culture supernatant to precipitate phages. The precipitated phages were suspended in PBS. This phage stock solution and a series of two-fold dilutions with PBS were used in phage ELISA.

3) Phage ELISA

Each target molecule or each negative control protein (hEphA2 for BSA used as a target molecule, and BSA for any of the other proteins used as a target molecule) was added to a Maxisorp plate and solid-phase immobilized overnight at 4° C. The TACI mutant-displaying phages prepared in the paragraphs 1) and 2) of Example 2 were added to this Maxisorp plate with the solid-phase immobilized target protein or negative control protein, and reacted for 2 hours. The Maxisorp plate was washed with Tris buffered saline containing 0.05% Tween-20 (hereinafter, referred to as TBST). Then, HRP/Anti-M13 Monoclonal Conjugate (manufactured by GE Healthcare Japan Corp.) (hereinafter, referred to as an "Anti-M13 antibody") diluted 5000-fold was added thereto. After washing with TBST again, the amount of a phage bound with the target molecule was detected as absorbance at a wavelength of 405 nm using ELISA POD Substrate A.B.T.S. Kit (manufactured by Nacalai Tesque, Inc.) (hereinafter, referred to as "ELISA POD").

As shown in FIGS. 1(A), 1(B), and 1(C), TACI mutant(s) binding to each target molecule was screened for or enriched from the randomly mutated TACI_d2 library by the panning operation.

Example 4

Comparison of Specificity Between Wild-Type TACI_d2 and hEphA2-Binding TACI_d2 Mutant 1) Preparation of Phage for Use in Phage ELISA As to 3 clones (α-EphA2 #1 to #3: corresponding to SEQ ID NOs: 3 to 5, respectively, in the Sequence Listing and to Nos. 2 to 4, respectively in FIG. 4) selected from the *Escherichia coli* colonies after the final round of panning with hEphA2 as a target molecule, an *Escherichia coli* suspension with $OD_{600\,nm}$=0.3 was prepared using 2×YT/Amp/1% Glu. The *Escherichia coli* cells of each clone were shake-cultured at 37° C. and allowed to grow until $OD_{600\,nm}$=0.5. A sufficient amount of helper phages M13K07 was added thereto to infect the cells at 37° C. for 30 minutes. After addition of 2×YT/Amp/Kan/0.25 mM IPTG, the helper phage-infected *Escherichia coli* was shake-cultured overnight at 22° C. 20% PEG/2.5 M NaCl solution was added to the recovered culture supernatant to precipitate phages. The precipitated phages were suspended in PBS. This phage stock solution and a series of two-fold dilutions with PBS were used in phage ELISA. An *Escherichia coli* TG-1 strain having a pCANTAB 5E vector containing the wild-type TACI_d2 gene was also subjected to the same operation as above to prepare phages.

2) Phage ELISA

Each of hEphA2, BSA, Recombinant Human BAFF/BLyS/TNFSF13B (R&D systems, Inc.; a polypeptide consisting of amino acids from Ala at position 134 to Leu at position 285 in human BAFF (UniProtKB/Swiss-Prot Accession # Q9Y275) and containing an N-terminally linked histidine tag, etc.; hereinafter referred to as "hBAFF"), and Recombinant Mouse EphA2/Fc Chimera, CF (R&D systems, Inc.; a polypeptide consisting of amino acids from Ala at position 22 to Ala at position 535 in mouse EphA2 (NCBI Accession No. #AAA82113) and containing a C-terminally linked Fc region (from Pro at position 100 to Lys at position 330) of human immunoglobulin G1 (hereinafter, referred to as "hIgG1"); hereinafter, referred to as "mEphA2/Fc") was added to a Maxisorp plate and solid-phase immobilized overnight at 4° C. TACI_d2 mutant-displaying phages were added to these Maxisorp plates and reacted for 2 hours. Each Maxisorp plate was washed with TBST. Then, an Anti-M13 antibody diluted 5000-fold was added thereto. After washing of the Maxisorp plate with TBST again, the amount of a phage bound with the protein solid-phase immobilized on the plate was detected as absorbance at a wavelength of 405 nm using ELISA POD.

Figure 2:
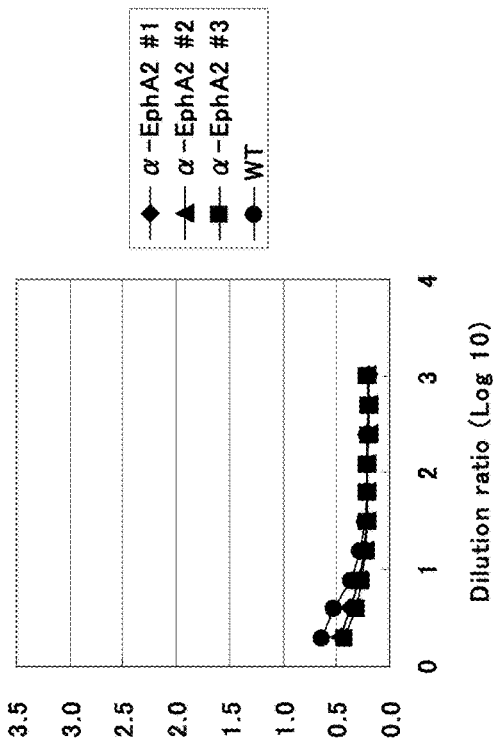
FIG. 2(A) is a diagram showing the comparison of specificity among TACI_d2 mutants #1 to #3 binding to recombinant human EphA2 (hereinafter, referred to as α-EphA2 TACI_d2 #1 to #3) and wild-type TACI_d2. hEphA2 and BSA were used as solid-phase immobilized proteins for FIGS. 2(A)(1) and 2(A)(2), respectively.
FIG. 2(B) is a diagram showing the comparison of specificity among TACI_d2 mutants #1 to #3 binding to recombinant human EphA2 (hereinafter, referred to as α-EphA2 TACI_d2 #1 to #3) and wild-type TACI_d2. hBAFF and mEphA2/Fc were used as solid-phase immobilized proteins for FIGS. 2(B)(3) and 2(B)(4), respectively.
Figure 2:
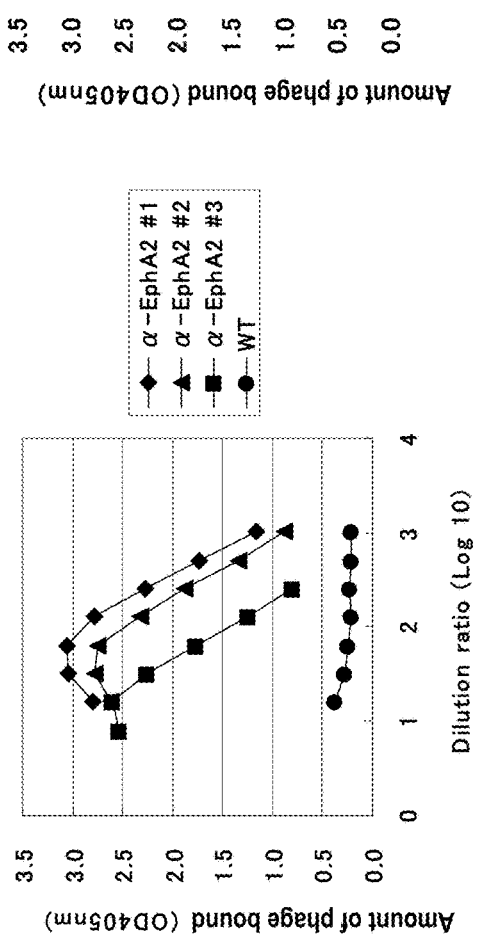
Figure 2:
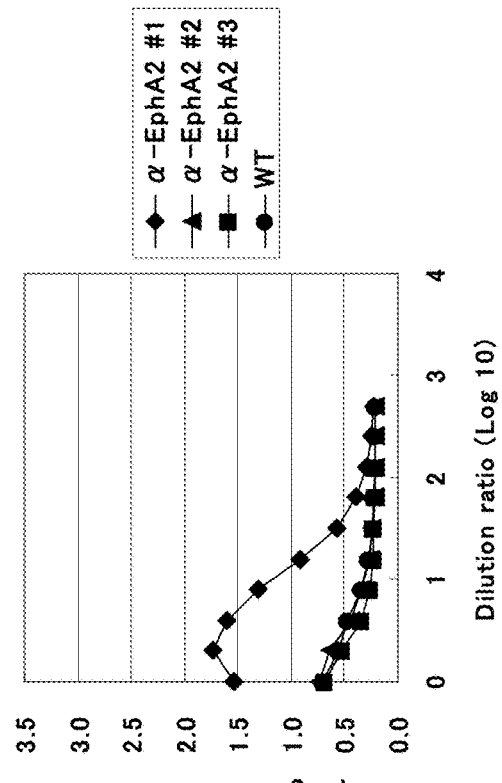
Figure 2:
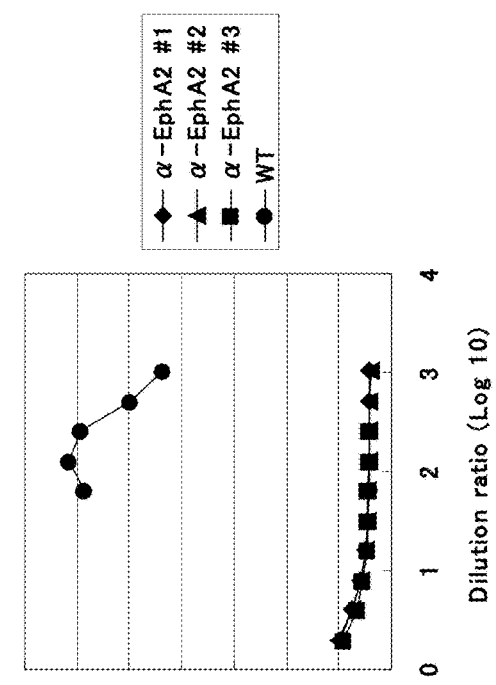

The results are shown in FIGS. 2(A) and 2(B). α-EphA2 #1 to #3 were obtained as TACI_d2 mutants binding to hEphA2. All of these α-EphA2 #1 to #3 lost the ability of wild-type TACI_d2 to bind to the endogenous ligand hBAFF. α-EphA2 #2 and #3 exhibited cross reactivity to mEphA2 at a level equivalent to wild-type TACI_d2, whereas α-EphA2 #1 had stronger cross reactivity.

Example 5

Confirmation of Binding of hEphA2-Binding TACI_d2 Mutant to Human EphA2-Expressing Cell 1) Cell Culture and Medium Human embryonic kidney cells (HEK293T cells) were cultured at 37° C. in the presence of 5% CO$_2$ using a Dulbecco's modified eagle's medium (hereinafter, referred to as "DMEM"; manufactured by GIBCO, Life Technologies Corp.) containing 10% fetal bovine serum (FBS) (hereinafter, this medium is referred to as "DMEM-10% FBS"). For use in transfection or flow cytometry, the cells were dissociated from the plate for culture using 0.05% trypsin-EDTA (GIBCO), and the cell suspension was then centrifuged to recover cells, which were then resuspended in DMEM-10% FBS and used.

2) Transfection

The HEK293T cells were transfected with a pcDNA-DEST40 Gateway vector (manufactured by Invitrogen Corp.) having an insert of the human EphA2 gene or the human ErbB2 gene as a negative control using Lipofectamine 2000 (manufactured by Invitrogen Corp.) according to the instructions.

3) Preparation of Cell

The transfected cells were recovered. The recovered cells were suspended in a FACS buffer (PBS containing 5% FBS) and applied to a nylon mesh. The solution was dispensed in an amount of 5×10$^5$ cells/well to 96 Well Cell Culture Cluster Round Bottom With Lid (manufactured by Costar, Corning Inc.) and centrifuged to remove a supernatant. The phage stock solution prepared in the paragraph 1) of Example 4 was added to the resulting cells at a concentration of 50 μL/well, and the mixture was left standing at 4° C. for 30 minutes. A FACS buffer was added thereto at a concentration of 150 μL/well, and the mixture was centrifuged to remove a supernatant. Again, a FACS buffer was added thereto at a concentration of 200 μL/well, and the mixture was centrifuged to remove a supernatant (hereinafter, cells were washed in the same way as this operation). An Anti-M13 antibody diluted 100-fold was added to the obtained cells at a concentration of 50 μL/well as a primary antibody, and the mixture was left standing at 4° C. for 30 minutes, followed by washing of the cells. Subsequently, FLUORESCEIN-CONJUGATED GOAT IGG FRACTION TO MOUSE IGG (manufactured by Cappel, MP Biomedicals, LLC) diluted 1000-fold was added thereto as a secondary antibody, and the mixture was left standing at 4° C. for 30 minutes, followed by washing of the cells. The obtained cells were suspended in 250 μL of a FACS buffer and subjected to Cytomics FC 500 Flow Cytometry System (manufactured by Beckman Coulter, Inc.). Fluorescently stained cells were detected.

Figure 3:
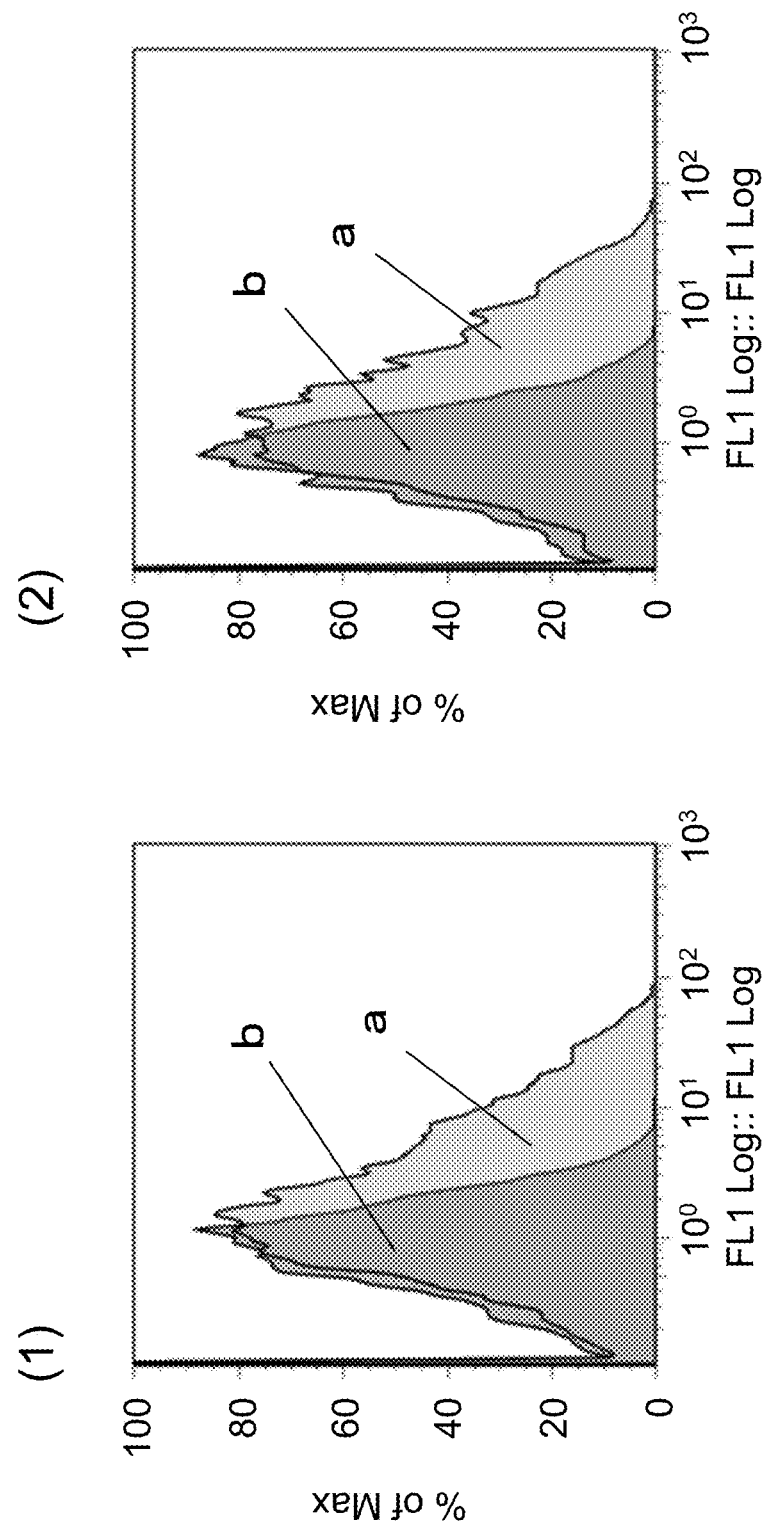
FIG. 3(A) is a diagram showing the comparison of binding activity against human EphA2-expressing cells between α-EphA2 TACI_d2 #1 and #2.
FIG. 3(B) is a diagram showing the comparison of binding activity against human EphA2-expressing cells between α-EphA2 TACI_d2 #3 and wild-type TACI_d2.
Figure 3:
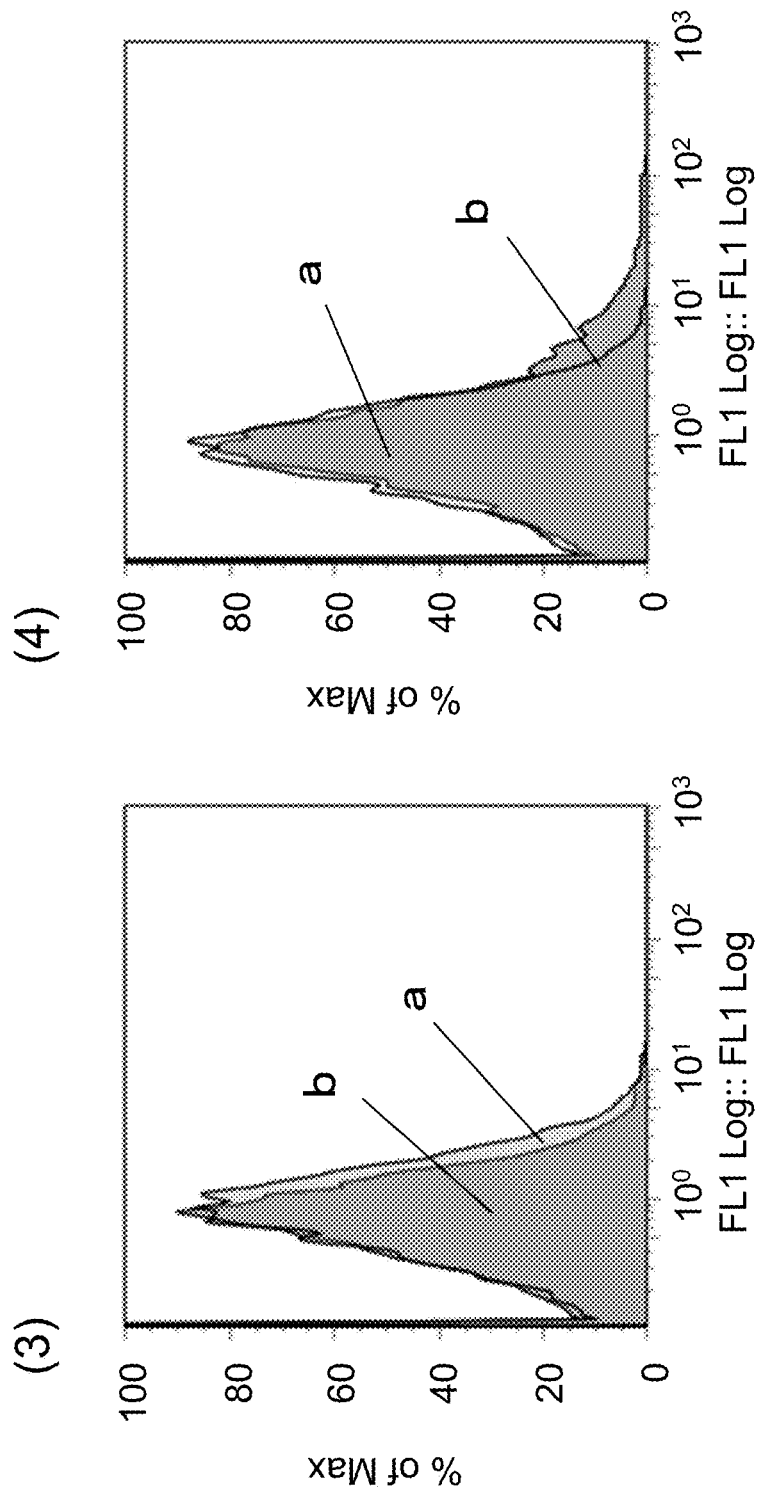

The results are shown in FIGS. 3(A) and 3(B). α-EphA2 #1 and #2 bound to not only recombinant hEphA2 but human EphA2 expressed on cell surface.

Example 6

Sequencing of TACI_d2 Mutants Binding to Various Target Molecules

As to TACI_d2 mutant peptides confirmed to bind to various target molecules in the same way as in the paragraphs 2) and 3) of Example 3, *Escherichia coli* expressing each of the peptides was isolated and cultured overnight at 37° C. using a 2×YT medium. A pCANTAB 5E vector having an insert of a gene encoding the peptide was prepared from the recovered *Escherichia coli* using QIAGEN Plasmid Mini Kit (manufactured by QIAGEN N.V.). The vector was sequenced using a pCANTAB-S1 primer (5'-CAACG-TAAAAAATTATTATTCGC-3': SEQ ID NO: 21 in the Sequence Listing).

The hBAFF described above was used as an endogenous TACI-binding molecule.

(1) Epidermal Growth Factor Receptor (EGFR)

A TACI_d2 mutant binding to the extracellular domain of human EGFR was screened for, and the obtained peptides were analyzed for their amino acid sequences.

The human EGFR used was a fusion protein (hEGFR/Fc described above) of the EGFR extracellular domain (from Leu at position 25 to Ser at position 645 in UniProtKB/Swiss-Prot Accession # P00533) and an hIgG1 Fc region (from Pro at position 100 to Lys at position 330).

The amino acid sequences of the obtained 3 peptides are shown in SEQ ID NOs: 6 to 8 in the Sequence Listing (Nos. 5 to 7 in FIG. 4).

(2) Vascular Endothelial Growth Factor (VEGF)

The VEGF used was a human isoform VEGF165 (CAS Registry File Registry Number 1217406-67-1; hVEGF described above).

A TACI_d2 mutant binding to human VEGF was screened for, and the obtained 6 peptides were analyzed for their amino acid sequences. As a result, the amino acid sequences were as shown in SEQ ID NOs: 9 to 14 in the Sequence Listing (Nos. 8 to 13 in FIG. 4).

(3) Tumor Necrosis Factor α (TNF-α)

The TNF-α used was human TNF (CAS Registry File Registry Number 1228062-30-3; hTNF-α described above).

A TACI_d2 mutant binding to human TNFα was screened for, and the obtained 3 peptides were analyzed for their amino acid sequences. As a result, the amino acid sequences were as shown in SEQ ID NOs: 15 to 17 in the Sequence Listing (Nos. 14 to 16 in FIG. 4).

(4) In all of the target molecule-binding TACI_d2 mutants obtained in the preceding paragraphs (1) to (3), Phe at position 78 within the TACI_d2 structure, i.e., at position 11 of SEQ ID NO: 1 in the Sequence Listing, was substituted by a different amino acid.

Example 7

Determination of Dissociation Constant of VEGF-Binding TACI_d2 Mutant for VEGF The gene of the hVEGF-binding TACI_d2 mutant (No. 9 in FIG. 4: SEQ ID NO: 10 in the Sequence Listing) obtained in Example 2 was amplified by PCR and inserted to a vector pET-32a for expression in *Escherichia coli* (Novagen, Merck KGaA). An *Escherichia coli* Origami™ B strain (Merck KGaA) was transformed with this vector and shake-cultured at 37° C. until $OD_{600\ nm}$=0.7. IPTG was added thereto at a final concentration of 1 mM to induce the expression of the mutant. Then, the bacterium was shake-cultured at 16° C. for 12 hours or longer. The cultured *Escherichia coli* was disrupted by ultrasonication and centrifuged. The obtained supernatant was applied to a HisTALON™ column (Clontech Laboratories, Inc.) for purification. Since the expressed mutant was thioredoxin-tagged and His-tagged, these tags were removed by cleavage using a Thrombin cleavage capture kit and application to a HisTALON™ column again. The purified mutant was subjected to size exclusion chromatography (Superdex 75 HR 10/30 column, GE Healthcare Japan Corp.). A peak corresponding to the molecular weight of the mutant (monomer) was recovered and subjected to affinity analysis. The affinity of the mutant was determined by a surface plasmon resonance method using Biacore 3000 (GE Healthcare Japan Corp.). The mutant was applied at various concentrations to hVEGF immobilized on a sensor chip. The dissociation constant of the mutant for hVEGF was determined from the obtained sensorgram. As a result, the mutant had a dissociation constant of 14 μM for hVEGF.

INDUSTRIAL APPLICABILITY

The peptide library of the present invention is useful in screening for a peptide binding to a target molecule.

FREE TEXT OF SEQUENCE LISTING

SEQ ID NO: 3—Amino acid sequence of human EphA2-binding peptide α-EphA2 #1

SEQ ID NO: 4—Amino acid sequence of human EphA2-binding peptide α-EphA2 #2

SEQ ID NO: 5—Amino acid sequence of human EphA2-binding peptide α-EphA2 #3

SEQ ID NO: 6—Amino acid sequence of human EGFR-binding peptide (1)

SEQ ID NO: 7—Amino acid sequence of human EGFR-binding peptide (2)

SEQ ID NO: 8—Amino acid sequence of human EGFR-binding peptide (3)

SEQ ID NO: 9—Amino acid sequence of human VEGF-binding peptide (1)

SEQ ID NO: 10—Amino acid sequence of human VEGF-binding peptide (2)

SEQ ID NO: 11—Amino acid sequence of human VEGF-binding peptide (3)

SEQ ID NO: 12—Amino acid sequence of human VEGF-binding peptide (4)

SEQ ID NO: 13—Amino acid sequence of human VEGF-binding peptide (5)

SEQ ID NO: 14—Amino acid sequence of human VEGF-binding peptide (6)

SEQ ID NO: 15—Amino acid sequence of human TNFα-binding peptide (1)

SEQ ID NO: 16—Amino acid sequence of human TNFα-binding peptide (2)

SEQ ID NO: 17—Amino acid sequence of human TNFα-binding peptide (3)

SEQ ID NO: 18—Nucleotide sequence of randomly mutated TACI_d2 oligonucleotide

SEQ ID NO: 19—Nucleotide sequence of PCR primer Primer Forward 1

SEQ ID NO: 20—Nucleotide sequence of PCR primer Primer Reverse 1

SEQ ID NO: 21—Nucleotide sequence of pCANTAB-S1 primer as primer for sequencing

The invention claimed is:

1. A peptide library comprising a plurality of randomly mutated peptides, wherein each mutant peptide has the amino acid sequence represented by SEQ ID NO: 1 in the sequence listing, wherein each amino acid at the 1st Xaa to the 11th Xaa of SEQ ID NO: 1 counting from the amino terminus is one of the following amino acids in approximately equal frequencies within the library: Ala, Glu, Gln, Asp, Asn, His, Trp, Arg, Lys, Val, Leu, Ile, Phe, Tyr, Ser, Met, Gly, and Thr, but is not cysteine or proline, and wherein the peptide library comprises at least one mutated peptide selected from the group consisting of:

(a) a peptide which binds to EphA2 (ephrin type-A receptor 2) and has the sequence of SEQ ID NO: 2, 3, or 4;
(b) a peptide which binds to EGFR-Fc (epidermal growth factor receptor-Fc receptor) and has the sequence of SEQ ID NO: 5, 6, or 7;
(c) a peptide which binds VEGF (vascular endothelial growth factor) and has the sequence of SEQ ID NOs: 8, 9, 10, 11, 12, or 13; and
(d) a peptide which binds TNF-α (tumor necrosis factor alpha) and has the sequence of SEQ ID NO: 14, 15, or 16.

2. The library according to claim 1, wherein each mutant peptide is prepared by a method comprising the following steps: (a) culturing a cell harboring a nucleic acid, or a vector comprising said nucleic acid, said nucleic acid encoding the amino acid sequence of mutant peptide of claim 1; and (b) recovering the peptide from the culture obtained in step (a).

3. The library according to claim 1, wherein each mutant peptide as a phenotype is linked directly or indirectly to a nucleic acid as a genotype corresponding to the phenotype.

4. The library according to claim 1, further comprising a nucleic acid selected from the group consisting of: (i) a nucleic acid comprising a nucleic acid consisting of a nucleotide sequence encoding the amino acid sequence of a peptide according to claim 1; (ii) a nucleic acid comprising a nucleotide sequence encoding the amino acid sequence of a peptide according to claim 1; and (iii) a nucleic acid consisting of a nucleotide sequence encoding the amino acid sequence of a peptide according to claim 1.

5. The library according to claim 1, wherein the library is a phage display library, a ribosome display library, or a nucleic acid display library.

* * * * *